US009163268B2

(12) United States Patent
Wendisch et al.

(10) Patent No.: US 9,163,268 B2
(45) Date of Patent: Oct. 20, 2015

(54) METHOD FOR FERMENTATIVELY PREPARING L-AMINO ACIDS

(75) Inventors: Volker F. Wendisch, Bielefeld (DE); Steffen Lindner, Moers (DE); Brigitte Bathe, Salzkotten (DE); Wilfried Claes, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 101 days.

(21) Appl. No.: 13/379,654

(22) PCT Filed: Jun. 18, 2010

(86) PCT No.: PCT/EP2010/058599
§ 371 (c)(1),
(2), (4) Date: Mar. 18, 2012

(87) PCT Pub. No.: WO2010/149574
PCT Pub. Date: Dec. 29, 2010

(65) Prior Publication Data
US 2012/0164698 A1    Jun. 28, 2012

(30) Foreign Application Priority Data

Jun. 25, 2009   (DE) .................. 10 2009 030 342

(51) Int. Cl.
| C12P 13/04 | (2006.01) |
| C12P 13/08 | (2006.01) |
| C12P 13/22 | (2006.01) |
| C12P 13/12 | (2006.01) |
| C12P 13/06 | (2006.01) |
| C12N 1/20 | (2006.01) |
| C12N 1/00 | (2006.01) |
| C12N 15/00 | (2006.01) |
| C07H 21/04 | (2006.01) |
| C12N 9/12 | (2006.01) |

(52) U.S. Cl.
CPC .............. *C12P 13/08* (2013.01); *C12N 9/1205* (2013.01); *C12Y 207/01023* (2013.01)

(58) Field of Classification Search
None
See application file for complete search history.

(56) References Cited

U.S. PATENT DOCUMENTS

| 4,278,765 | A | | 7/1981 | Debabov et al. |
| 4,346,170 | A | | 8/1982 | Sano et al. |
| 5,175,107 | A | | 12/1992 | Debabov et al. |
| 5,250,423 | A | | 10/1993 | Murakami et al. |
| 5,756,345 | A | | 5/1998 | Camakaris et al. |
| 5,830,716 | A | * | 11/1998 | Kojima et al. ................. 435/106 |
| 5,939,295 | A | | 8/1999 | Dunkak et al. |
| 6,783,967 | B2 | | 8/2004 | Moeckel et al. |
| 2007/0059744 | A1 | * | 3/2007 | Pompejus et al. ................. 435/6 |
| 2009/0029356 | A1 | * | 1/2009 | Pompejus et al. ................. 435/6 |
| 2009/0311758 | A1 | | 12/2009 | Jessberger et al. |

FOREIGN PATENT DOCUMENTS

| EP | 1 108 790 A2 | 6/2001 |
| EP | 1 717 616 A1 | 11/2006 |
| FR | 2 511 032 | 2/1983 |
| WO | WO 2006/001616 A1 | 1/2006 |
| WO | WO 2006/100211 A1 | 9/2006 |
| WO | WO 2007/011939 A2 | 1/2007 |
| WO | WO 2007/113127 A1 | 10/2007 |
| WO | WO 2008/082211 A1 | 7/2008 |
| WO | WO 2009/141330 A1 | 11/2009 |

OTHER PUBLICATIONS

International Search Report for PCT/EP2010/058599 filed Jun. 18, 2010.
Written Opinion of the International Searching Authority for PCT/EP2010/058599 filed Jun. 18, 2010.
International Preliminary Examination Report for PCT/EP2010/058599 filed Jun. 18, 2010.
Letter dated Nov. 8, 2011 filed for PCT/EP2010/058599 with Applicants' informal comments on the Written Opinion.
Database Geneseq;*Corynebacterium glutamicum* MCP protein SEQ ID No. 2324; Database accession No. AED72148; XP002596662.
Database Uniprot; Database accession No. A4QE06; XP002596663.
Blattner, et al., "The Complete Genome Sequence of *Escherichia coli* K-12," *Science* 277(5331):1453-74 (Sep. 1997).
Cerdeno-Tarraga, et al., "The complete genome sequence and analysis of *Corynebacterium diphtheriae* NCTC13129," *Nucleic Acids Research* 31(22):6516-6523 (2003).
Follmann, et al., "Functional genomics of pH homeostasis in *Corynebacterium glutamicum* revealed novel links between pH response, oxidative stress, iron homeostasis and methionine synthesis," *BMC Genomics* 10:621-644 (2009).
Garavaglia, et al., "Allosteric Regulation of *Bacillus subtilis* NAD Kinase by Quinolinic Acid," *Journal of Bacteriology* 185(16):4844-4850 (Aug. 2003).
Georgi, et al., "Lysine and glutamate production by *Corynebacterium glutamicum* on glucose, fructose and sucrose: Roles of malic enzyme and fructose-1,6-biphosphatase," *Metabolic Engineering* 7:291-301 (2005).

(Continued)

*Primary Examiner* — Iqbal H Chowdhury
(74) *Attorney, Agent, or Firm* — Law Office of: Michael A. Sanzo, LLC

(57) ABSTRACT

The invention relates to a method for preparing organic-chemical compounds, characterized in that the following steps are carried out: a) fermentation of a microorganism secreting an L-amino acid, which microorganism contains an overexpressed polynucleotide coding for a polypeptide having polyphosphate-dependent $NAD^+$ kinase activity, in a fermentation medium, to form a fermentation broth, b) accumulation of said compound in said fermentation broth and/or in the cells of said microorganism. The invention relates to a method for preparing organic-chemical compounds by fermentation of a microorganism in which a polypeptide having polyphosphate-dependent $NAD^+$ kinase is overexpressed.

20 Claims, 2 Drawing Sheets

(56) References Cited

OTHER PUBLICATIONS

Ikeda, et al., "The *Corynebacterium glutamicum* genome: features and impacts on biotechnological processes," *Appl Microbiol Biotechnol* 62:99-109 (2003).

Kalinowski, et al., "The complete *Corynebacterium glutamicum* ATCC 13032 genome sequence and its impact on the production of L-aspartate-derived amino acids and vitamins," *Journal of Biotechnology* 104(1-3):5-25 (2003).

Kawai, et al., "Establishment of a Mass-Production System for NADP Using Bacterial Inorganic Polyphosphate/ATP-NAD Kinase," *Journal of Bioscience and Bioengineering* 92(5):447-452 (2001).

Kawai, et al., "Inorganic Polyphosphate/ATP-NAD Kinase of *Micrococcus flavus* and *Mycobacterium tuberculosis* H37Rv," *Biochemical and Biophysical Research Communications* 276:57-63 (2000).

Li, et al., "Overexpression of NAD kinase in recombinant *Escherichia coli* harboring the *phbCAB* operon improves poly(3-hydroxybutyrate) production," *Appl Microbiol Biotechnol* 83:939-947 (2009).

Lindner, et al., "Polyphosphate/ATP-dependent NAD kinase of *Corynebacterium glutamicum*: biochemical properties and impact of *ppnK* overexpression on lysine production," *Appl Microbiol Biotechnol* 87:583-593 (2010).

McGuinness, et al., "NAD+kinase-A review," *International J Biochem* 17:1-11 (1985).

Menkel, et al., "Influence of Increased Aspartate Availability on Lysine Formation by a Recombinant Strain of *Corynebacterium glutamicum* and Utilization of Fumarate," *Applied and Environmental Microbiology* 55(3):684-688 (Mar. 1989).

Murata, et al., "Continuous production of NADP by immobilized *Brevibacterium ammoniagenes* cells," *Biotechnology and Bioengineering* 21(5):887-895 (1979).

Nishio, et al., "Comparative Complete Genome Sequence Analysis of the Amino Acid Replacements Responsible for the Thermostability of *Corynebacterium efficiens*," *Genome Research* 13(7):1572-1579 (2003).

Sakuraba, et al., "First Archaeal Inorganic Polyphosphate/ATP-Dependent NAD Kinase, from Hyperthermophilic Archaeon *Pyrococcus horikoshii*: Cloning, Expression, and Characterization," *Applied and Environmental Microbiology* 71(8):4352-4358 (Aug. 2005).

Silberach, et al., "Adaptation of *Corynebacterium glutamicum* to Ammonium Limitation: a Global Analysis Using Transcriptome and Proteome Techniques," *Applied and Environmental Microbiology* 71(5):2391-2402 (May 2005).

Tauch, et al., "Complete Genome Sequence and Analysis of the Multiresistant Nosocomial Pathogen *Corynebacterium jeikeium* K411, a Lipid-Requiring Bacterium of the Human Skin Flora," *Journal of Bacteriology* 187(13):4671-4682 (Jul. 2005).

Yukawa, et al., "Comparative analysis of the *Corynebacterium glutamicum* group and complete genome sequence of strain R," *Microbiology* 153:1042-1058 (2007).

English Language abstract for FR 2 511 032, listed as document B3 above.

\* cited by examiner

```
Cg_Ppnk_AA    MTAPTNAG------------------ELRRVLLVPHTGRSSNIESAILAAKLLDDAGI
Ce_Ppnk_AA    MTETT---------------------ERIVLLVPHTGRSSNIESAVLAAEHLDRAGI
Cd_Ppnk_AA    MTIDCHE-------------------DRRVLLVPHTGRPQNVASAALAAELLDDSGV
Cj_Ppnk_AA    MTTFGTDHNADQGADSGDKATKAASGAQTEREVLLVAHTGVHENLGLAAEAASRLQKGGI
              **           * **** ***      *      *   **    *       *

Cg_Ppnk_AA    DVRVLINDADDPIAEHSVLGRFTHVRHAADAADGAELVLVLGGDGTFLRAADMAHAVDLP
Ce_Ppnk_AA    TVRVLVNEEDDPIKTHPVLGRFEHVIHSRTAAEGAELVLVLGGDGTFLRAADLAHAVDLP
Cd_Ppnk_AA    GVRVLVPAEDTTVATHPVLGQFERVSHSPQATQSVDLVLVLGGDGTFLRAADLAHGADLP
Cj_Ppnk_AA    NVRVMATADPAPVARHEVLGRFKRFGHTKEAATGVEMVIVLGGDGTFLRAADIAHSADVP
               ***          * *** *   *  *        * ************* *   *

Cg_Ppnk_AA    VLGINLGHVGFLAEWESDSLEEALKRVIDRDYRIEDRMTLTVVVLDGGGEEIGRGWALNE
Ce_Ppnk_AA    VLGINLGHVGFLAEWESDSLEDAVKRVIDCDYRVEDRMTLDVIVRDSDLEVIGRGWALNE
Cd_Ppnk_AA    VLGINLGHVGFLAEWEKDSLDEAVRRVTKGSFRIEERMTLDVSVYDSNGTAIGRGWALNE
Cj_Ppnk_AA    VLGINMGHIGFLAEWEQESLQEAVDRVIDRDYRIEDRMTLSITARDMDGRVLGTGWALNE
              ***** **  *******  ** **  **  *        *            * ******

Cg_Ppnk_AA    VSIENLNRRGVLDATLEVDARPVASFGCDGVLISTPTGSTAYAFSAGGPVLWPELDAILV
Ce_Ppnk_AA    VSVENLNRRGVLDATLEVDFRPVASFGCDGVLISTPTGSTAYAFSAGGPVLWPELDAILV
Cd_Ppnk_AA    VSIENSNRSGVLDATLEIDSRPVSSFGCDGIIVSTPTGSTAYAFSAGGPVLWPELDAILV
Cj_Ppnk_AA    CSVENLNRQGVLDTILEVDERPVSSFGCDGVLVSTPTGSTAYAFSAGGPVLWPELDAILV
               * ** ** **** ** * *** ****** * ***************************

Cg_Ppnk_AA    VPNNAHALFTKPLVVSPKSTVAVESNSDTSAAMAVMDGFRPIPMPPGSRVEVTRGERPVR
Ce_Ppnk_AA    VPNNAHALFTKPLVVSPRSTVAVESMSGTSPAMAVMDGFRPIPMPPGSRVEIVRGKRPVR
Cd_Ppnk_AA    VPNNAHALFTKPLVVSPRSSVAVESHPSAFPATAVMDGFRSISVPPGARVEVKRGSRSIK
Cj_Ppnk_AA    VTSNAHTLFSRPLVVSPNSMVAVETNPSTSPATVVMDGFRQIHMPPGARVEIRRGPQPVR
              *  *** **  ******  * ****  *    ** ******  * *** *** ***  **

Cg_Ppnk_AA    WVRLDSSPFTDRLVSKLRLPVTGWRGPQKQAENKDPRSAG--
Ce_Ppnk_AA    WVRLDSLPFTDRLVHKLRLPVVGWRGPDKQKELLDAETPDQP
Cd_Ppnk_AA    WVRLDDIPFTDRLVTKLRLPVEGWRGPKNMIPQINPHSA---
Cj_Ppnk_AA    WVRLDSAPFTDRLVHKFRLPVTGWRGPRH------------
              *****  ******* * **** ****
```

Figure 1

```
Cg_Ppnk_AA      MTAPTNAGELRRVLLVPHTGRSSNIESAILAAKLLDDAGIDVRVLINDADDPIAEHSVLG
CgR_PpnK_AA     MTAPTNAGELRRVLLVPHTGRSSNIESAILAAKLLDDAGIDVRVLINDADDPIAEHPVLG
Bf_PpnK_AA      MTASTNAGELRRVLLVPHTGRSSNIESAILAAKLLDDAGIDVRVLINDADDPIAEHPVLG
                ***.*******************************************************.***

Cg_Ppnk_AA      RFTHVRHAADAADGAELVLVLGGDGTFLRAADMAHAVDLPVLGINLGHVGFLAEWESDSL
CgR_PpnK_AA     RFTHVRHAADAAEGAELVLVLGGDGTFLRAADMAHAVDLPVLGINLGHVGFLAEWESDSL
Bf_PpnK_AA      RFTHVRHAADAADGAELVLVLGGDGTFLRAADMAHAVDLPVLGINLGHVGFLAEWESDSL
                ************ ***********************************************

Cg_Ppnk_AA      EEALKRVIDRDYRIEDRMTLTVVVLDGGGEEIGRGWALNEVSIENLNRRGVLDATLEVDA
CgR_PpnK_AA     EEALKRVIDRDYRIEDRMTLTVVVLDGGGEEIGRGWALNEVSIENLNRRGVLDATLEVDA
Bf_PpnK_AA      EEALKRVIDRDYRIEDRMTLNVVVLDGGGEEIGRGWALNEVSIENLNRRGVLDATLEVDA
                ******************** ***************************************

Cg_Ppnk_AA      RPVASFGCDGVLISTPTGSTAYAFSAGGPVLWPELDAILVVPNNAHALFTKPLVVSPKST
CgR_PpnK_AA     RPVASFGCDGVLISTPTGSTAYAFSAGGPVLWPELDAILVVPNNAHALFTKPLVVSPKST
Bf_PpnK_AA      RPVASFGCDGVLISTPTGSTAYAFSAGGPVLWPELDAILVVPNNAHALFTKPLVVSPKST
                ************************************************************

Cg_Ppnk_AA      VAVESNSDTSAAMAVMDGFRPIPMPFGSRVEVTRGERPVRWVRLDSSPFTDRLVSKLRLP
CgR_PpnK_AA     VAVESNSDTSAAMAVMDGFRPIPMPFGSRVEVTRGERPVRWVRLDSSPFTDRLVSKLRLP
Bf_PpnK_AA      VAVESNSDTSAAMAVMDGFRPIPMPFGSRVEVTRGERPVRWVRLDSSPFTDRLVSKLRLP
                ************************************************************

Cg_Ppnk_AA      VTGWRGPQKQAENKDPRSAG
CgR_PpnK_AA     VTGWRGPQKQAENKDPRSAG
Bf_PpnK_AA      VTGWRGPQKQAENKDPRSAG
                ********************
```

Figure 2

METHOD FOR FERMENTATIVELY PREPARING L-AMINO ACIDS

CROSS REFERENCE TO RELATED APPLICATIONS

The present application is US national stage of international application, PCT/EP2010/058599 which had an international filing date of Jun. 18, 2010 and which was published in English under PCT Article 21(2) on Dec. 29, 2010. Priority is claimed to German application DE 10 2009 030 342.1, filed on Jun. 25, 2009, which is hereby incorporated by reference in its entirety.

PRIOR ART

L-amino acids are used in human medicine, in the pharmaceutical industry, in the food industry and very particularly in animal nutrition.

It is known that L-amino acids such as, for example, L-lysine, are prepared by fermentation of strains of coryneform bacteria, in particular *Corynebacterium glutamicum*, or of strains of the Enterobacteriaceae family, in particular *Escherichia coli*. Because of the great economic importance, work is continually being done on improving the preparation methods. Method improvements may relate to fermentation technology measures such as, for example, stirring and supplying oxygen, or to the composition of the nutrient media, for example the sugar concentration during fermentation, or to the working-up to product form by, for example, ion exchange chromatography or to the intrinsic performance properties of the microorganism itself.

The methods used for improving the performance properties of these microorganisms are those of mutagenesis, selection and choice of mutants. The strains obtained in this way are resistant to anti-metabolites or are auxotrophic for metabolites of regulatory importance, and produce L-amino acids. A known anti-metabolite is the lysine analogue S-(2-aminoethyl)-L-cysteine (AEC).

Methods of recombinant DNA technology have likewise been used for some years for strain improvement of L-amino acid-producing strains of the genus *Corynebacterium*, in particular *Corynebacterium glutamicum*, or of the genus *Escherichia*, in particular *Escherichia coli*, by modifying, i.e. enhancing or attenuating, individual amino acid biosynthesis genes and investigating the effect on amino acid production.

The nucleotide sequences of the chromosomes of numerous bacteria have been disclosed.

The nucleotide sequence of the *Corynebacterium glutamicum* ATCC13032 genome is described in Ikeda and Nakagawa (Applied Microbiology and Biotechnology 62, 99-109 (2003)), in EP 1 108 790 and in Kalinowski et al. (Journal of Biotechnology 104(1-3), (2003)).

The nucleotide sequence of the *Corynebacterium glutamicum* R genome is described in Yukawa et al. (Microbiology 153(4):1042-1058 (2007)).

The nucleotide sequence of the *Corynebacterium efficiens* genome is described in Nishio et al (Genome Research. 13 (7), 1572-1579 (2003)).

The nucleotide sequence of the *Corynebacterium diphteriae* NCTC 13129 genome has been described by Cerdeno-Tarraga et al. (Nucleic Acids Research 31 (22), 6516-6523 (2003)).

The nucleotide sequence of the *Corynebacterium jeikeum* genome has been described by Tauch et al. (Journal of Bacteriology 187 (13), 4671-4682 (2005)).

The nucleotide sequence of the *Escherichia coli* K-12 genome has been published by Blattner et al. (Science 277 (5331), 1453-74 (1997)).

A review of various aspects of the fermentative production of L-amino acids can be found in R. Faurie and J. Thommel in Advances in Biochemical Engineering Biotechnology, Volume 79 (Springer-Verlag, Berlin, Heidelberg (Germany) 2003).

OBJECT OF THE INVENTION

It is an object of the invention to provide novel methods for fermentatively preparing L-amino acids.

DESCRIPTION OF THE INVENTION

The invention relates to a method for preparing organic-chemical compounds or products containing these compounds, characterized in that the following steps are carried out:

a) Fermentation of a microorganism secreting an organic-chemical compound, which microorganism contains an overexpressed, preferably recombinantly overexpressed, polynucleotide coding for a polypeptide having polyphosphate-dependent $NAD^+$ kinase activity, in a fermentation medium, to form a fermentation broth.

b) Accumulation of said compound in said fermentation broth and/or in the cells of said microorganism.

For the measures of the invention, an organic-chemical compound means a vitamin such as, for example, thiamine (vitamin B1), riboflavin (vitamin B2), cyanocobalamin (vitamin B12), folic acid (vitamin M), tocopherol (vitamin E) or nicotinic acid/nicotinamide, a nucleoside or nucleotide such as, for example, S-adenosylmethionine, inosine-5'-monophosphoric acid and guanosine-5'-monophosphoric acid, L-amino acids or else an amine such as cadaverine, for example.

Preference is given to preparing L-amino acids and products containing them.

The term L-amino acids comprises the proteinogenic amino acids, and also L-ornithine and L-homoserine. Proteinogenic L-amino acids mean the L-amino acids present in natural proteins, i.e. in proteins of microorganisms, plants, animals and humans. The proteinogenic amino acids include L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and, where appropriate, L-selenocysteine and L-pyrrolysine. Preference is given to the L-amino acids L-lysine, L-methionine, L-threonine and L-tryptophan. Particular preference is given to L-lysine and L-threonine. Very particular preference is given to L-lysine.

The term amino acids or L-amino acids, where mentioned hereinbelow, also comprises salts thereof, for example lysine mono-hydrochloride or lysine sulphate in the case of the amino acid L-lysine.

The term microorganism comprises bacteria, yeasts and fungi. Bacteria which may be mentioned are in particular the genus *Bacillus*, the genus *Corynebacterium*, the genus *Streptomyces*, and bacteria of the Enterobacteriacae family.

Within the genus *Corynebacterium*, preference is given to strains based on the following species:

*Corynebacterium efficiens*, for example the type strain DSM44549,

*Corynebacterium glutamicum*, for example the type strain ATCC13032 or the strain R, and

*Corynebacterium ammoniagenes*, for example the strain ATCC6871,
with very particular preference being given to the species *Corynebacterium glutamicum*.

Some representatives of the species *Corynebacterium glutamicum* are also known in the prior art under other names. These include for example:
strain ATCC13870, referred to as *Corynebacterium acetoacidophilum*,
strain DSM20137, referred to as *Corynebacterium lilium*,
strain ATCC17965, referred to as *Corynebacterium melassecola*,
Strain ATCC14067, referred to as *Brevibacterium flavum*,
strain ATCC13869, referred to as *Brevibacterium lactofermentum*, and
strain ATCC14020, referred to as *Brevibacterium divaricatum*.

The term "Micrococcus glutamicus" for *Corynebacterium glutamicum* has likewise been in use.

Some representatives of the species *Corynebacterium* have also been referred to in the prior art as *Corynebacterium thermoaminogenes*, for example the strain FERM BP-1539.

Within the Enterobacteriacae family, preference is given to the genera *Escherichia*, *Erwinia*, *Providencia*, *Pantoea* and *Serratia*. Particular preference is given to the genera *Escherichia* and *Serratia*. Very particular preference is given to the species *Escherichia coli* in the genus *Escherichia* and to the species *Serratia marcescens* in the genus *Serratia*.

The microorganisms or strains (starting strains) employed for the measures of overexpressing the polyphosphate-dependent NAD$^+$ kinase preferably already have the ability to concentrate the desired L-amino acid(s) in the cell or secrete them into the nutrient medium surrounding them and accummulate them there. The term "produce" is also used for this hereinbelow. More specifically, the strains employed for said overexpression measures have the ability to concentrate or accumulate in the cell or in the nutrient medium ≥ (at least) ≥0.10 g/l, 0.25 g/l, ≥0.5 g/l, ≥1.0 g/l, ≥1.5 g/l, ≥2.0 g/l, ≥4 g/l or ≥10 g/l of the desired compound in ≤ (at most) 120 hours, ≤96 hours, ≤48 hours, ≤36 hours, ≤24 hours or ≤12 hours. The starting strains are preferably strains which have been produced by mutagenesis and selection, by recombinant DNA techniques or by a combination of both methods.

It is obvious and requires no further explanation that a microorganism suitable for the measures of the invention can also be obtained by firstly overexpressing a polyphosphate-dependent NAD+ kinase in a wild strain such as, for example, in the *Corynebacterium glutamicum* type strain ATCC 13032 or in the strain ATCC 14067, and subsequently causing said microorganism, by further genetic measures described in the prior art, to produce the desired L-amino acid(s). Transforming the wild type only with the polynucleotide mentioned does not constitute an inventive measure.

Examples of strains of the species *Corynebacterium glutamicum* which secrete or produce L-lysine are:
*Corynebacterium glutamicum* MH20-22B (=DSM16835) described in Menkel et al. (Applied and Environmental Microbiology 55(3), 684-688 (1989)) and deposited as DSM16835,
*Corynebacterium glutamicum* DM1729 described in Georgi et al. (Metabolic Engineering 7, 291-301 (2005)) and in EP 1 717 616 A2 and deposited as DSM17576, and
*Corynebacterium glutamicum* DSM13994 described in U.S. Pat. No. 6,783,967.

An example of an L-lysine-secreting or -producing strain of the species *Corynebacterium efficiens* is:
*Corynebacterium thermoaminogenes* AJ12521 (=FERM BP-3304) described in U.S. Pat. No. 5,250,423.

Examples of strains of the species *Escherichia coli* which secrete or produce L-lysine are:
*Escherichia coli* pDA1/TOC21R (=CNCM I-167) described in FR-A-2511032, and
*Escherichia coli* NRRL B-12199 described in U.S. Pat. No. 4,346,170.

L-Lysine-producing microorganisms typically have a feedback-resistant or desensitized aspartate kinase. Feedback-resistant aspartate kinases mean aspartate kinases (LysC) which, by comparison with the wild form (wild type), show less sensitivity to inhibition by mixtures of lysine and threonine or mixtures of AEC (aminoethylcysteine) and threonine or lysine alone or AEC alone. The genes or alleles coding for these aspartate kinases which are desensitized by comparison with the wild type are also referred to as lysC$^{FBR}$ alleles. Numerous lysC$^{FBR}$ alleles coding for aspartate kinase variants which have amino acid substitutions by comparison with the wild-type protein are described in the prior art. The lysC gene in bacteria of the genus *Corynebacterium* is also referred to as ask gene. The aspartate kinase encoded by the lysC gene in Enterobacteriaceae is also referred to as aspartokinase III.

An extensive list containing information about the amino acid substitutions in the *Corynebacterium glutamicum* aspartate kinase protein that result in desensitization is included inter alia in the German patent application with the application number PCT/EP2009/056046. Preference is given to aspartate kinase variants carrying the following amino acid substitutions selected from the group consisting of: L-isoleucine for L-threonine in position 380 of the amino acid sequence and optionally L-phenylalanine for L-serine in position 381, L-isoleucine for L-threonine in position 311 and L-threonine for L-alanine in position 279.

An extensive list containing information about the amino acid substitutions in the *Escherichia coli* aspartate kinase III protein that result in desensitization to inhibition by L-lysine is included inter alia in the EP 0 834 559 A1 on page 3 (lines 29 to 41). Preference is given to an aspartate kinase variant containing L-aspartic acid instead of glycine in position 323 of the amino acid sequence and/or L-isoleucine instead of L-methionine in position 318.

An example of a strain of the species *Corynebacterium glutamicum* which secretes or produces L-methionine is
*Corynebacterium glutamicum* DSM 17322 described in WO 2007/011939.

Examples of strains of the species *Escherichia coli* which secrete or produce L-methionine are
*Escherichia coli* KCCM-10818P described in WO 2008/082211, and
*Escherichia coli* KCCM-10568 described in WO 2006/001616.

Examples of strains of the species *Escherichia coli* which secrete or produce L-tryptophan are:
*Escherichia coli* JP4735/pMU3028 described in U.S. Pat. No. 5,756,345, and
*Escherichia coli* JB102/p5LRPS2 described in U.S. Pat. No. 5,939,295.

Examples of strains of the species *Escherichia coli* which produce or secrete L-threonine are:
*Escherichia coli* VNIIgenetika MG442 described in U.S. Pat. No. 4,278,765, and
*Escherichia coli* BKIIM B-3996 described in U.S. Pat. No. 5,175,107.

Cadaverine-producing or -secreting microorganisms are described, for example, in WO 2007/113127.

A polypeptide having polyphosphate-dependent NAD⁻ kinase activity means a polypeptide or protein which catalyzes phosphorylation of NAD⁺ (nicotinamide-adenine dinucleotide) to give NADP⁺ (nicotinamide-adenine dinucleotide phosphate), with polyphosphate being utilized as donor of the phosphoryl or phosphate group.

Polyphosphates denote the linear condensation products of salts of ortho-phosphoric acid ($H_3PO_4$). Polyphosphates in their simplest form are the salts of the pentabasic triphosphoric acid ($H_5P_3O_{10}$) which consists of a chain of three phosphate units. The salts of the hexabasic tetraphosphoric acid have a chain length of four phosphate units. Details regarding the chemistry of polyphosphates can be found in chemistry textbooks such as, for example, the "Lehrbuch der anorganischen Chemie" ["Textbook of inorganic chemistry"] (A. F. Hollemann and E. Wiberg, Walter De Gruyter & Co., Berlin, 1971).

The polyphosphate-dependent NAD⁺ kinases which can be employed for the measures of the invention are capable of utilizing linear polyphosphates with a chain length of ≥ (at least) 3, ≥4, ≥5, ≥6, ≥7, ≥8, ≥9, ≥10, ≥12, ≥14, ≥16, ≥18, ≥20, ≥25, ≥30, ≥40 phosphate units. In some cases, polyphosphates with a chain length of from 45 to 65 or 65 to 75 phosphate units are also utilized.

A gene coding for a polyphosphate-dependent NAD⁺ kinase is referred to as ppnK. The gene name means polyphosphate-dependent NAD kinase (the letters used for said gene name are underlined). In some cases, polyphosphate-dependent NAD⁺ kinases are also capable of utilizing ATP as donor of the phosphoryl group. From a chemical point of view, a gene is a polynucleotide.

Public databases such as, for example, the UniProtKB (Universal Protein Resource Knowledgebase) database describe the polyphosphate-dependent NAD+ kinases of a large variety of organisms. The UniProtKB database is maintained by the UniProt consortium which includes the European Bioinformatics Institute (EBI, Wellcome Trust, Hinxton, Cambridge, United Kingdom), the Swiss Institute of Bioinformatics (SIB, Centre Medical Universitaire, Geneva, Switzerland) and the Protein Information Resource (PIR, Georgetown University, Washington, D.C., US).

Examples of polyphosphate-dependent NAD⁺ kinases described in the literature are those of *Pyrococcus horikoshii* (Sakuraba et al., Applied and Environmental Microbiology 71:4352-4358 (2005)), *Mycobacterium tuberculosis* (Kawai et al., Biochemical and Biophysical Research Communications 276:57-632 (2000)), *Bacillus subtilis* (Garavaglia et al., Journal of Bacteriology 185:4844-50 (2003)), *Thermotoga maritima* (McGuinness and Butler International Journal of Biochemistry 17:1-11 (1985)) and *Brevibacterium ammoniagenes* (Murata et al., Biotechnology and Bioengineering. 21(5):887-895 (1979)).

The polyphosphate-dependent NAD+ kinase genes may be isolated from the organisms with the aid of the polymerase chain reaction (PCR) using suitable primers. Instructions can be found inter alia in the laboratory manual "PCR" by Newton and Graham (Spektrum Akademischer Verlag, Heidelberg, Germany, 1994) and in WO 2006/100211 on pages 14 to 17.

The gene of any polyphosphate-dependent NAD⁺ kinase may be employed for the measures of the invention. Preference is given to employing genes coding for polypeptides having polyphosphate-dependent NAD⁺ kinase activity, the amino acid sequences of which are ≥ (at least) ≥50%, ≥60%, ≥70%, ≥80%, ≥90%, ≥92%, ≥94%, ≥96%, ≥97%, ≥98%, ≥99%, identical to the amino acid sequence of SEQ ID NO:2.

FIG. 1 depicts an alignment of the PpnK polypeptide amino acid sequences of representatives of various species of the genus *Corynebacterium*, namely *Corynebacterium glutamicum* ATCC13032, *Corynebacterium efficiens* YS-314, *Corynebacterium diphteriae* NCTC 13129 and *Corynebacterium jeikeum* K411. The PpnK polypeptide amino acid sequence of *C. efficiens* is 81.3% identical, that of *C. diphteriae* is 69.3% identical, and that of *C. jeikeum* is 61.7% identical to the PpnK polypeptide amino acid sequence of *C. glutamium* ATCC13032 depicted in SEQ ID NO:2.

FIG. 2 depicts an alignment of the PpnK polypeptide amino acid sequences of various representatives or strains of the species *Corynebacterium glutamicum*, namely strain ATCC 13032, strain R and strain ATCC 14067. The three amino acid sequences differ by amino acid substitutions in three positions.

The amino acid sequence of the polyphosphate-dependent NAD⁺ kinase of ATCC 14067 is novel. Accordingly, the invention relates to an isolated polynucleotide, preferably having the nucleotide sequence of SEQ ID NO:3, which codes for a polypeptide having polyphosphate-dependent NAD⁺ kinase enzyme activity and comprises the amino acid sequence of SEQ ID NO:4. In this context, the invention furthermore relates to a factor containing the isolated polynucleotide, and to a microorganism containing said vector or said isolated polynucleotide or containing said polypeptide having polyphosphate-dependent NAD+ kinase enzyme activity in an overexpressed form.

The amino acid sequence of the polyphosphate-dependent NAD+ kinase of ATCC 13869 is likewise novel. Accordingly, the invention relates to an isolated polynucleotide, preferably having the nucleotide sequence of SEQ ID NO:5, which codes for a polypeptide having polyphosphate-dependent NAD⁺ kinase enzyme activity and comprises the amino acid sequence of SEQ ID NO:6. In this context, the invention furthermore relates to a factor containing the isolated polynucleotide, and to a microorganism containing said vector or said isolated polynucleotide or containing said polypeptide having polyphosphate-dependent NAD+ kinase enzyme activity in an overexpressed form.

The PpnK polypeptide amino acid sequences of various microorganisms, as set forth in FIGS. 1 and 2, can be found in the databases of the National Center for Biotechnology Information (NCBI, Bethesda, Md., US). They are accessible there under the following accession numbers:

| Name of microorganism: | Accession number: |
|---|---|
| *Corynebacterium diphtheriae* NCTC 13129: | NC_002935 |
| *Corynebacterium glutamicum* R: | NC_009342 |
| *Corynebacterium jeikeium* K411: | NC_007164 |
| *Corynebacterium glutamicum* ATCC 13032: | NC_006958 |

The alignments of amino acid sequences, as depicted in FIGS. 1 and 2, were generated using the program ClustalX 1.83 developed by Thompson et al. (Nucleic Acids Research, 25, 4876-4882 (1997)). The parameters were set as follows: pwmatrix=gonnet; pwgapopen=10.00; pwgapext=0.10; matrix=blosum; gapopen=10.00; gapext=0.20; maxdiv=30; endgaps; novgap; hgapresidues=GPSNDQEKR; gapdist=4; outorder=aligned; interactive.

Similarly, it is also possible to employ other programs available in the prior art, such as, for example, the program "Align Plus for Windows version 3 (1997)", which is sold by Scientific & Educational Software Cary (NC, US) and is based on the work by Altschul et al. (Journal of Molecular Biology 215 (3), 403-410 (1990)).

Particular preference is given to employing genes coding for polypeptides having polyphosphate-dependent $NAD^+$ kinase activity, the amino acid sequence of which contains one or more of the features selected from the group consisting of
- a) amino acid sequence according to SEQ ID NO:2,
- b) amino acid sequence according to SEQ ID NO:2, including one or more, at most 30, 25, 20, 15, 10, 5, 4, 2, or 1 deletion(s) of amino acids,
- c) amino acid sequence according to SEQ ID NO:2, including one or more, at most 30, 25, 20, 15, 10, 5, 4, 2, or 1 insertion(s) of amino acids, and
- d) amino acid sequence according to SEQ ID NO:2, including one or more, at most 140, 130, 120, 110, 100, 90, 80, 70, 60, 50, 40, 30, 25, 20, 15, 10, 5, 4, 2, or 1 substitution(s) of amino acids.

Particular preference is given to employing, for a method according to the invention using bacteria of the genus *Corynebacterium*, genes coding for polypeptides having polyphosphate-dependent $NAD^+$ kinase activity, the amino acid sequence of which contains one or more of the features selected from the group consisting of
- a) amino acid sequence according to SEQ ID NO:2,
- b) amino acid sequence according to SEQ ID NO:2, including one or more, at most 25, 20, 15, 10, 5, 4, 2, or 1 deletion(s) of amino acids,
- c) amino acid sequence according to SEQ ID NO:2, including one or more, at most 25, 20, 15, 10, 5, 4, 2, or 1 insertion(s) of amino acids, and
- d) amino acid sequence according to SEQ ID NO:2 including one or more, at most 140, 130, 120, 110, 100, 90, 80, 70, 60, 50, 40, 30, 25, 20, 15, 10, 5, 4, 3, 2, or 1, preferably at most 5, 4, 3, 2, or 1, substitution(s) of amino acids.

Where appropriate, preference is given to conservative amino acid substitutions. In the case of aromatic amino acids, conservative substitutions are those in which phenylalanine, tryptophan and tyrosine are substituted for each other. In the case of hydrophobic amino acids, conservative substitutions are those in which leucine, isoleucine and valine are substituted for one another. In the case of polar amino acids, conservative substitutions are those in which glutamine and asparagine are substituted for one another. In the case of basic amino acids, conservative substitutions are those in which arginine, lysine and histidine are substituted for one another. In the case of acidic amino acids, conservative substitutions are those in which aspartic acid and glutamic acid are substituted for one another. In the case of the amino acids containing hydroxyl groups, conservative substitutions are those in which serine and threonine are substituted for one another.

It is furthermore possible to use polynucleotides which hybridize under stringent conditions with the nucleotide sequence complementary to SEQ ID NO:1, preferably to the coding region of SEQ ID NO:1, and code for a polypeptide having polyphosphate-dependent $NAD^+$ kinase enzyme activity.

Instructions regarding the hybridization of nucleic acids or polynucleotides can be found by the skilled worker inter alia in the manual "The DIG System Users Guide for Filter Hybridization" from Boehringer Mannheim GmbH (Mannheim, Germany, 1993) and in Liebl et al. (International Journal of Systematic Bacteriology 41: 255-260 (1991)). Hybridization takes place under stringent conditions, that is to say only hybrids in which the probe, i.e. a polynucleotide comprising the nucleotide sequence complementary to SEQ ID NO:1, preferably the coding region of SEQ ID NO:1, and the target sequence, i.e. the polynucleotides treated with or identified by said probe, are at least 70% identical are formed. The stringency of the hybridization, including the washing steps, is known to be influenced or determined by varying the buffer composition, temperature and salt concentration. The hybridization reaction is generally carried out with relatively low stringency compared with the washing steps (Hybaid Hybridisation Guide, Hybaid Limited, Teddington, UK, 1996).

For example, a 5×SSC buffer at a temperature of approx. 50° C.-68° C. may be employed for the hybridization reaction. Here, probes may also hybridize with polynucleotides which are less than 70% identical to the nucleotide sequence of the probe employed. Such hybrids are less stable and are removed by washing under stringent conditions. This may be achieved, for example, by lowering the salt concentration to 2×SSC or 1×SSC and, where appropriate, subsequently 0.5× SSC (The DIG System User's Guide for Filter Hybridisation, Boehringer Mannheim, Mannheim, Germany, 1995), with a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being set. Preference is given to temperature ranges of approx. 64° C.-68° C. or approx. 66° C.-68° C. It is optionally possible to lower the salt concentration to a concentration corresponding to 0.2× SSC or 0.1×SSC. The SSC buffer optionally contains sodium dodecylsulphate (SDS) at a concentration of 0.1%. By gradually increasing the hybridization temperature in steps of approx. 1-2° C. from 50° C. to 68° C., it is possible to isolate polynucleotide fragments which are at least 70%, at least 80%, at least 90%, at least 92%, at least 94%, at least 96%, at least 97%, at least 98%, or at least 99%, where appropriate 100%, identical to the sequence or complementary sequence of the probe employed and which code for a polypeptide having polyphosphate-dependent NAD+ kinase enzyme activity. Further instructions regarding hybridization are obtainable on the market in the form of "kits" (e.g. DIG Easy Hyb from Roche Diagnostics GmbH, Mannheim, Germany, Catalogue No. 1603558).

For the measures of the invention, a ppnK gene coding for a polyphosphate-dependent $NAD^+$ kinase is overexpressed in a microorganism or starting or parent strain producing the desired amino acid(s).

The studies resulting in the present invention likewise established that overexpression of the NADH kinase present in Saccharomyces cerevisiae, which uses NADH to give NADPH by using ATP as donor of the phosphoryl group, in suitable L-amino acid producers results in an increase in amino acid production.

It was furthermore established that overexpression of the ATP-dependent of the $NAD^+$ kinase present in *Escherichia coli* in suitable L-amino acid producers results in an increase in amino acid production.

Overexpression generally means an increase in the intracellular concentration or activity of a ribonucleic acid, of a protein (polypeptide) or of an enzyme by comparison with the starting strain (parent strain) or wild-type strain, if the latter is the starting strain. A starting strain (parent strain) means the strain on which the measure leading to overexpression has been carried out.

For overexpression, preference is given to the methods of recombinant overexpression. These include all methods in which a microorganism is prepared using a DNA molecule provided in vitro. Examples of such DNA molecules include promoters, expression cassettes, genes, alleles, coding regions, etc. They are transferred by methods of transformation, conjugation, transduction or similar methods into the desired microorganism.

The measures of overexpression increase the activity or concentration of the corresponding polypeptides generally by at least 10%, 25%, 50%, 75%, 100%, 150%, 200%, 300%, 400% or 500%, preferably at most by 1000%, 2000%, 4000%, 10000% or 20000%, based on the activity or concentration of said polypeptide in the strain prior to the measure resulting in overexpression.

Overexpression is achieved by a multiplicity of methods available in the prior art. These include increasing the copy number and modifying the nucleotide sequences directing or controlling expression of the gene. The transcription of a gene is controlled inter alia by the promoter and optionally by proteins which suppress (repressor proteins) or promote (activator proteins) transcription. The translation of the RNA formed is controlled inter alia by the ribosome binding site and the start codon. Polynucleotides or DNA molecules which include a promoter and a ribosome binding site and optionally a start codon are also referred to as expression cassette.

The copy number may be increased by means of plasmids which replicate in the cytoplasm of the microorganism. To this end, an abundance of plasmids are described in the prior art for very different groups of microorganisms, which plasmids can be used for setting the desired increase in the copy number of the gene. Plasmids suitable for the genus *Escherichia* are described, for example, in the manual Molecular Biology, Labfax (Ed.: T. A. Brown, Bios Scientific, Oxford, UK, 1991). Plasmids suitable for the genus *Corynebacterium* are described, for example, in Tauch et al. (Journal of Biotechnology 104 (1-3), 27-40, (2003)), or in Stansen et al. (Applied and Environmental Microbiology 71, 5920-5928 (2005)).

The copy number may furthermore be increased by at least one (1) copy by introducing further copies into the chromosome of the microorganism. Methods suitable for the genus *Corynebacterium* are described, for example, in the patents WO 03/014330, WO 03/040373 and WO 04/069996. Examples of methods suitable for the genus *Escherichia* are insertion of a gene copy into the att site of the phage (Yu and Court, Gene 223, 77-81 (1998)), chromosomal amplification with the aid of the phage Mu, as described in EP 0 332 448, or the methods of gene replacement with the aid of conditionally replicating plasmids, as described by Hamilton et al. (Journal of Bacteriology 174, 4617-4622 (1989)) or Link et al. (Journal of Bacteriology 179, 6228-6237 (1997)).

Gene expression may furthermore be increased by using a strong promoter which is functionally linked to the gene to be expressed. Preference is given to using a promoter which is stronger than the natural promoter, i.e. the one present in the wild type or parent strain. To this end, the prior art has an abundance of methods available.

Promoters suitable for the genus *Corynebacterium* can be found inter alia in Morinaga et al. (Journal of Biotechnology 5, 305-312, (1987)), in the patent documents EP 0 629 699 A2, US 2007/0259408 A1 (gap promoter), WO 2006/069711, EP 1 881 076 A1 and EP 1 918 378 A1 (sod promoter) and in reviews such as the "Handbook of *Corynebacterium glutamicum*" (Eds.: Lothar Eggeling and Michael Bott, CRC Press, Boca Raton, US (2005)) or the book "*Corynebacteria, Genomics and Molecular Biology*" (Ed.: Andreas Burkovski, Caister Academic Press, Norfolk, UK (2008)). Examples of promoters which allow controlled, i.e. inducible or repressible, expression are described, for example, in Tsuchiya and Morinaga (Bio/Technology 6, 428-430 (1988)).

Promoters suitable for the genus *Escherichia* have been known for a long time. They include, inter alia, the classical promoters lac promoter, trp promoter, the hybrid promoters tac and trc, the $P_L$ and $P_R$ promoters of phage $\lambda$. Similarly, it is possible to use the promoters of the T7 phage, the gearbox promoters, the nar promoter or the promoters of the genes rrsG, rnpB, csrA, csrB, ompA, fusA, pepQ, rplX or rpsG. Controlled expression is permitted, for example, by the cI857-$P_R$ or the cI857-$P_L$ system of the $\lambda$ phage (Götting et al., BioTechniques 24, 362-366 (1998)). Reviews can be found in Makrides (Microbiological Reviews 60(3), 512-538 (1996)) or in the manual "*Escherichia coli* and *Salmonella*, Cellular and Molecular Biology" (F. C. Neidhardt (Editor in Chief), ASM Press, Washington, US (1996)).

Such promoters or expression cassettes are typically employed at a distance of from 1 to 1000, preferably 1 to 500, nucleotides upstream of the first nucleotide of the start codon of the coding region of the gene.

It is likewise possible to place a plurality of promoters upstream of the desired gene or functionally link them to the gene to be expressed and in this way achieve increased expression.

The structure of *Escherichia coli* promoters is well known. It is therefore possible to increase the strength of a promoter by modifying its sequence by means of one or more substitution(s) and/or one or more insertion(s) and/or one or more deletion(s) of nucleotides. Examples of this can be found inter alia in "Herder Lexikon der Biologie" (Spektrum Akademischer Verlag, Heidelberg, Germany (1994)).

The structure of the *Corynebacterium glutamicum* and *Escherichia coli* ribosome binding sites is likewise well known and is described, for example, in Amador (Microbiology 145, 915-924 (1999)), and in manuals and textbooks of genetics, for example "Gene und Klone" (Winnacker, Verlag Chemie, Weinheim, Germany (1990)) or "Molecular Genetics of Bacteria" (Dale and Park, Wiley and Sons Ltd., Chichester, UK (2004)).

Overexpression can likewise be achieved by increasing the expression of activator proteins or reducing or switching off the expression of repressor proteins.

The overexpression measures mentioned may be combined with one another in a suitable manner. Thus it is possible, for example, to combine the use of a suitable promoter with increasing the copy number.

Instructions regarding the handling of DNA, digestion and ligation of DNA, transformation and selection of transformants can be found inter alia in the known manual" by Sambrook et al. "Molecular Cloning: A Laboratory Manual, Second Edition (Cold Spring Harbor Laboratory Press, 1989).

The extent of expression or overexpression can be determined by measuring the amount of the mRNA transcribed from the gene, by determining the amount of the polypeptide and by determining the enzyme activity.

The amount of mRNA may be determined inter alia by using the methods of "Northern blotting" and of quantitative RT-PCR. Quantitative RT-PCR involves reverse transcription preceding the polymerase chain reaction. For this, the LightCycler™ system from Roche Diagnostics (Boehringer Mannheim GmbH, Roche Molecular Biochemicals, Mannheim, Germany) may be used, as described, for example, in Jungwirth et al. (FEMS Microbiology Letters 281, 190-197 (2008)). The concentration of the protein may be determined via 1- and 2-dimensional protein gel fractionation and subsequent optical identification of the protein concentration by appropriate evaluation software in the gel. A customary method of preparing protein gels for coryneform bacteria and of identifying said proteins is the procedure described by Hermann et al. (Electrophoresis, 22:1712-23 (2001)). The protein concentration may likewise be determined by Western blot hybridization using an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation using corresponding software for concentration determination (Lohaus and Meyer (1998) Biospektrum 5:32-39; Lottspeich, Angewandte Chemie 321: 2630-2647 (1999)).

The microorganisms produced may be cultured continuously—as described, for example, in WO 05/021772—or discontinuously in a batch process (batch cultivation) or in a fed batch or repeated fed batch process for the purpose of producing the desired organic-chemical compound. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium or medium are interchangeable.

It is possible to use, as carbon source, sugars and carbohydrates such as, for example, glucose, sucrose, lactose, fructose, maltose, molasses, sucrose-containing solutions from sugar beet or sugar cane processing, starch, starch hydrolysate and cellulose, oils and fats such as, for example, soybean oil, sunflower oil, groundnut oil and coconut fat, fatty acids such as, for example, palmitic acid, stearic acid and linoleic acid, alcohols such as, for example, glycerol, methanol and ethanol, and organic acids such as, for example, acetic acid or lactic acid.

It is possible to use, as nitrogen source, organic nitrogen-containing compounds such as peptones, yeast extract, meat extract, malt extract, corn steep liquor, soybean flour and urea, or inorganic compounds such as ammonium sulphate, ammonium chloride, ammonium phosphate, ammonium carbonate and ammonium nitrate. The nitrogen sources can be used individually or as mixture.

It is possible to use, as phosphorus source, phosphoric acid, potassium dihydrogen phosphate or dipotassium hydrogen phosphate or the corresponding sodium-containing salts.

The culture medium must additionally comprise salts, for example in the form of chlorides or sulphates of metals such as, for example, sodium, potassium, magnesium, calcium and iron, such as, for example, magnesium sulphate or iron sulphate, which are necessary for growth. Finally, essential growth factors such as amino acids, for example homoserine and vitamins, for example thiamine, biotin or pantothenic acid, may be employed in addition to the above-mentioned substances.

Said starting materials may be added to the culture in the form of a single batch or be fed in during the cultivation in a suitable manner.

The pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8. To control foaming, it is possible to employ antifoams such as, for example, fatty acid polyglycol esters.

To maintain the stability of plasmids, it is possible to add to the medium suitable selective substances such as, for example, antibiotics. The fermentation is preferably carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch processes, the cultivation is preferably continued until an amount of the desired organic-chemical compound sufficient for being recovered has formed. This aim is normally achieved within 10 hours to 160 hours. In continuous processes, longer cultivation times are possible. The activity of the microorganisms results in a concentration (accumulation) of the organic-chemical compound in the fermentation medium and/or in the cells of said microorganisms.

Example of suitable fermentation media can be found inter alia in the patents U.S. Pat. No. 5,770,409, U.S. Pat. No. 5,990,350, U.S. Pat. No. 5,275,940, WO 2007/012078, U.S. Pat. No. 5,827,698, WO 2009/043803, U.S. Pat. No. 5,756, 345 and U.S. Pat. No. 7,138,266.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC•GC (Magazine of Chromatographic Science) 7(6), 484-487 (1989)).

It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51: 1167-1174 (1979)).

Detection is carried out photometrically (absorption, fluorescence).

A review regarding amino acid analysis can be found inter alia in the textbook "Bioanalytik" from Lottspeich and Zorbas (Spektrum Akademischer Verlag, Heidelberg, Germany 1998).

The performance of the methods or fermentation processes according to the invention, in terms of one or more of the parameters selected from the group of concentration (compound formed per unit volume), yield (compound formed per unit carbon source consumed), formation (compound formed per unit volume and time) and specific formation (compound formed per unit dry cell matter or dry biomass and time or compound formed per unit cellular protein and time) or else other process parameters and combinations thereof, is increased by at least 0.5%, at least 1%, at least 1.5% or at least 2%, based on methods or fermentation processes using microorganisms containing non-overexpressed polyphosphate-dependent $NAD^+$ kinase.

The fermentation measures result in a fermentation broth which contains the desired organic-chemical compound, preferably L-amino acid.

A product containing the organic-chemical compound is then provided or produced or recovered in liquid or solid form.

A fermentation broth means a fermentation medium or nutrient medium in which a microorganism has been cultivated for a certain time and at a certain temperature. The fermentation medium or the media employed during fermentation comprise(s) all the substances or components which ensure production of the desired compound and typically propagation and viability.

When the fermentation is complete, the resulting fermentation broth accordingly comprises
- a) the biomass (cell mass) of the microorganism, said biomass having been produced due to propagation of the cells of said microorganism,
- b) the desired organic-chemical compound formed during the fermentation,
- c) the organic byproducts formed during the fermentation, and
- d) the constituents of the fermentation medium employed or of the starting materials, such as, for example, vitamins such as biotin or salts such as magnesium sulphate, which have not been consumed in the fermentation.

The organic byproducts include substances which are produced by the microorganisms employed in the fermentation in addition to the particular desired compound and are optionally secreted. These also include sugars such as, for example, trehalose.

The fermentation broth is removed from the culture vessel or fermentation tank, collected where appropriate, and used for providing a product containing the organic-chemical compound, preferably an L-amino acid-containing product, in liquid or solid form. The expression "Recovering the L-amino acid-containing product" is also used for this. In the simplest case, the L-amino acid-containing fermentation broth itself, which has been removed from the fermentation tank, constitutes the recovered product.

One or more of the measures selected from the group consisting of
- a) partial (>0% to <80%) to complete (100%) or virtually complete (≥80%, ≥90%, ≥95%, ≥96%, ≥97%, ≥98%, ≥99%) removal of the water,
- b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
- c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic byproducts formed during fermentation, and
- d) partial (>0%) to complete (100%) or virtually complete (≥80%, ≥90%, ≥95%, ≥96%, ≥97%, ≥98%, ≥99%, ≥99.3%, ≥99.7%) removal of the constituents of the fermentation medium employed or of the starting materials, which have not been consumed in the fermentation, from the fermentation broth achieves concentration or purification of the desired organic-chemical compound. Products having a desired content of said compound are isolated in this way.

The partial (>0% to <80%) to complete (100%) or virtually complete (≥80% to <100%) removal of the water (measure a)) is also referred to as drying.

In one variant of the method, complete or virtually complete removal of the water, of the biomass, of the organic byproducts and of the unconsumed constituents of the fermentation medium employed results in pure (≥80% by weight, ≥90% by weight) or high-purity (≥95% by weight, ≥97% by weight, ≥99% by weight) product forms of the desired organic-chemical compound, preferably L-amino acids. An abundance of technical instructions for measures a), b), c) and d) are available in the prior art.

In the case of the amino acid L-lysine, essentially four different product forms are known in the prior art.

One group of L-lysine-containing products includes concentrated aqueous alkaline solutions of purified L-lysine (EP-B-0534865). A further group, as described for example in U.S. Pat. No. 6,340,486 and U.S. Pat. No. 6,465,025, includes aqueous acidic biomass-containing concentrates of L-lysine-containing fermentation broths. The best-known group of solid products includes pulverulent or crystalline forms of purified or pure L-lysine, which is typically in the form of a salt such as, for example, L-lysine monohydrochloride. A further group of solid product forms is described for example in EP-B-0533039. The product form described therein comprises besides L-lysine most of the starting materials used during the fermentative production and not consumed and, where appropriate, the biomass of the microorganism employed with a proportion of >0%-100%.

A wide variety of processes appropriate for the various product forms are known for producing the L-lysine-containing product or the purified L-lysine from the fermentation broth.

The methods essentially used to produce pure solid L-lysine are those of ion exchange chromatography, where appropriate with use of activated carbon, and methods of crystallization. The corresponding base or a corresponding salt such as, for example, the monohydrochloride (Lys-HCl) or lysine sulphate ($Lys_2$-$H_2SO_4$) is obtained in this way.

EP-B-0534865 describes a process for producing aqueous basic L-lysine-containing solutions from fermentation broths. In the process described therein, the biomass is separated from the fermentation broth and discarded. A base such as, for example, sodium hydroxide, potassium hydroxide or ammonium hydroxide is used to set a pH of between 9 to 11. The mineral constituents (inorganic salts) are removed from the broth by crystallization after concentration and cooling and are either used as fertilizer or discarded.

In processes for producing lysine by using bacteria of the genus *Corynebacterium*, preferred processes are those resulting in products which comprise constituents of the fermentation broth. These are used in particular as animal feed additives.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

In one procedure, the biomass is completely or virtually completely removed so that no (0%) or at most 30%, at most 20%, at most 10%, at most 5%, at most 1% or at most 0.1% biomass remains in the prepared product. In a further procedure, the biomass is not removed, or is removed only in small proportions, so that all (100%) or more than 70%, 80%, 90%, 95%, 99% or 99.9% biomass remains in the product prepared. In one method according to the invention, accordingly, the biomass is removed in proportions of from ≥0% to ≤100%.

Finally, the fermentation broth obtained after the fermentation can be adjusted, before or after the complete or partial removal of the biomass, to an acidic pH with an inorganic acid such as, for example, hydrochloric acid, sulphuric acid or phosphoric acid, or organic acids such as, for example, propionic acid (GB 1,439,728 or EP 1 331 220). It is likewise possible to acidify the fermentation broth with the complete content of biomass. Finally, the broth can also be stabilized by adding sodium bisulphite (NaHSO$_3$, GB 1,439,728) or another salt, for example ammonium, alkali metal or alkaline earth metal salt of sulphurous acid.

During the removal of the biomass, any organic or inorganic solids present in the fermentation broth are partially or completely removed. The organic byproducts dissolved in the fermentation broth, and the dissolved unconsumed constituents of the fermentation medium (starting materials), remain at least partly (>0%), preferably to an extent of at least 25%, particularly preferably to an extent of at least 50% and very particularly preferably to an extent of at least 75% in the product. Where appropriate, they also remain completely (100%) or virtually completely, meaning >95% or >98% or greater than 99%, in the product. If a product in this sense comprises at least part of the constituents of the fermentation broth, this is also described by the term "product based on fermentation broth".

Subsequently, water is removed from the broth, or it is thickened or concentrated, by known methods such as, for example, using a rotary evaporator, thin-film evaporator, falling-film evaporator, by reverse osmosis or by nanofiltration. This concentrated fermentation broth can then be worked up to free-flowing products, in particular to a fine powder or preferably coarse granules, by methods of freeze drying, spray drying, spray granulation or by other processes as described for example in the circulating fluidized bed according to PCT/EP2004/006655. A desired product is isolated where appropriate from the resulting granules by screening or dust removal.

It is likewise possible to dry the fermentation broth directly, i.e. without previous concentration by spray drying or spray granulation.

"Free-flowing" means powders which, from of a series of glass orifice vessels with orifices of different sizes, flow unimpeded at least out of the vessel with a 5 mm (millimeters) orifice (Klein: Seifen, Öle, Fette, Wachse 94, 12 (1968)).

"Fine" means a powder predominantly (>50%) having a particle size of diameter from 20 to 200 µm.

"Coarse" means a product predominantly (>50%) of a particle size of diameter from 200 to 2000 µm.

The particle size determination can be carried out by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine powder can in turn be converted by suitable compaction or granulation processes into a coarse, very free-flowing, storable and substantially dust-free product.

The term "dust-free" means that the product comprises only small proportions (<5%) of particle sizes below 100 µm in diameter.

"Storable" in the sense of this invention means a product which can be stored for at least one (1) year or longer, preferably at least 1.5 years or longer, particularly preferably two (2) years or longer, in a dry and cool environment without any substantial loss (at most 5%) of the respective amino acid occurring.

The invention further relates to a method described in principle in WO 2007/042363 A1. To this end, a method is carried out which uses the fermentation broth obtained according to the invention, from which the biomass has been removed completely or partially, where appropriate, and which comprises the following steps:
 a) the pH is reduced to 4.0 to 5.2, in particular 4.9 to 5.1, by adding sulphuric acid and a molar sulphate/L-lysine ratio of from 0.85 to 1.2, preferably 0.9 to 1.0, particularly preferably >0.9 to <0.95, is established in the broth, where appropriate by adding one or more further sulphate-containing compound(s), and
 b) the mixture obtained in this way is concentrated by removal of water, and granulated where appropriate, where one or both of the following measures is/are carried out where appropriate before step a):
 c) measurement of the molar sulphate/L-lysine ratio to ascertain the required amount of sulphate-containing compound(s)
 d) addition of a sulphate-containing compound selected from the group of ammonium sulphate, ammonium bisulphate and sulphuric acid in appropriate ratios.

Where appropriate, also before step b), a salt of sulphurous acid, preferably alkali metal bisulphite, particularly preferably sodium bisulphite, is added in a concentration of from 0.01 to 0.5% by weight, preferably 0.1 to 0.3% by weight, particularly preferably 0.1 to 0.2% by weight, based on the fermentation broth.

Preferred sulphate-containing compounds which should be mentioned in the context of the abovementioned process steps are in particular ammonium sulphate and/or ammonium bisulphate or appropriate mixtures of ammonia and sulphuric acid and sulphuric acid itself.

The molar sulphate/L-lysine ratio V is calculated by the formula: $V=2\times[SO_4^{2-}]/[\text{L-lysine}]$. This formula takes account of the fact that the $SO_4^{2-}$ anion is doubly charged, or sulphuric acid is dibasic. A ratio of V=1 means that a stoichiometric composition $Lys_2\text{-}(H_2SO_4)$ is present, whereas the finding with a ratio of V=0.9 is a 10% sulphate deficit and with a ratio of V=1.1 is a 10% sulphate excess.

It is advantageous to employ during the granulation or compaction the usual organic or inorganic auxiliaries or carriers such as starch, gelatine, cellulose derivatives or similar substances, as normally used in the processing of food products or feeds as binders, gelling agents or thickeners, or further substances such as, for example, silicas, silicates (EP0743016A) or stearates.

It is further advantageous to provide the surface of the resulting granules with oils or fats as described in WO 04/054381. Oils which can be used are mineral oils, vegetable oils or mixtures of vegetable oils. Examples of such oils are soybean oil, olive oil, soybean oil/lecithin mixtures. In the same way, silicone oils, polyethylene glycols or hydroxyethylcellulose are also suitable. Treatment of the surfaces with said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight, based on the total amount of the feed additive.

Preferred products have a proportion of ≥97% by weight with a particle size of from 100 to 1800 µm or a proportion of ≥95% by weight with a particle size of diameter 300 to 1800 µm. The proportion of dust, i.e. particles with a particle size <100 µm, is preferably >0 to 1% by weight, particularly preferably not exceeding 0.5% by weight.

However, alternatively, the product may also be absorbed on an organic or inorganic carrier known and customary in the processing of feeds, such as, for example, silicas, silicates, meals, brans, flours, starches, sugars or others, and/or be mixed and stabilized with customary thickeners or binders.

Examples of use and processes therefor are described in the literature (Die Mühle+Mischfuttertechnik 132 (1995) 49, page 817).

Finally, the product can also be brought, by coating processes with film-formers such as, for example, metal carbonates, silicas, silicates, alginates, stearates, starches, gums and cellulose ethers, as described in DE-C-4100920, into a state which is stable to digestion by animal stomachs, especially the stomach of ruminants.

To establish a desired L-lysine concentration in the product it is possible, depending on requirements, to add the L-lysine during the process in the form of a concentrate or, where appropriate, of a substantially pure substance or its salt in liquid or solid form. These can be added singly or as mixtures to the resulting or concentrated fermentation broth, or else during the drying or granulation process.

The invention further relates to a method for preparing a solid lysine-containing product, which method is described in principle in US 20050220933. This involves carrying out a method which uses the fermentation broth obtained according to the invention and which comprises the following steps:
  a) filtration of the fermentation broth, preferably with a membrane filter, to result in a biomass-containing slurry and a filtrate,
  b) concentration of the filtrate, preferably so as to result in a solids content of from 48 to 52% by weight,
  c) granulation of the concentrate obtained in step b), preferably at a temperature of from 50° C. to 62° C., and
  d) coating of the granules obtained in c) with one or more of the coating agent(s).

The coating agents preferably used for the coating in step d) are selected from the group consisting of
  d1) the biomass obtained in step a),
  d2) an L-lysine-containing compound, preferably selected from the group of L-lysine hydrochloride or L-lysine sulphate,
  d3) an essentially L-lysine-free substance with an L-lysine content of <1% by weight, preferably <0.5% by weight, preferably selected from the group of starch, carrageenan, agar, silicas, silicates, meals, brans and flours, and
  d4) a water-repellent substance, preferably selected from the group of oils, polyethylene glycols and liquid paraffins.

The L-lysine content is adjusted to a desired value by the measures corresponding to steps d1) to d4), in particular d1) to d3).

In the production of L-lysine-containing products, the ratio of the ions is preferably adjusted so that the molar ion ratio corresponding to the following formula $$2\times[SO_4^{2-}]+[Cl^-]-[NH_4^+]-[Na^+]-[K^+]-2\times[Mg^{2+}]-2\times[Ca^{2+}]/[L-Lys]$$

gives 0.68 to 0.95, preferably 0.68 to 0.90, particularly preferably 0.68 to 0.86, as described by Kushiki et al. in US 20030152633.

In the case of L-lysine, the solid product produced in this way has, based on the fermentation broth, a lysine content (as lysine base) of from 10% by weight to 70% by weight or 20% by weight to 70% by weight, preferably 30% by weight to 70% by weight and very particularly preferably from 40% by weight to 70% by weight, based on the dry matter of the product. Maximum lysine base contents of 71% by weight, 72% by weight, 73% by weight are likewise possible.

The water content of the L-lysine-containing solid product is up to 5% by weight, preferably up to 4% by weight, and particularly preferably less than 3% by weight.

The strain DM1729 was deposited with the German collection of Microorganisms and cell cultures under accession number DSM17576 on 16 Sep. 2005.

FIG. 1:

Comparison of the amino acid sequences (multiple sequence alignment) of the encoded PpnK polypeptides of various species of the genus *Corynebacterium*.

The abbreviations have the following meaning: Cg_PpnK_AA: PpnK amino acid sequence of *Corynebacterium glutamicum* ATCC 13032 (SEQ ID NO:2). Ce_Ppnk_AA: PpnK amino acid sequence of *Corynebacterium efficiens* YS-314 (SEQ ID NO:9). Cd_Ppnk_AA: PpnK amino acid sequence of *Corynebacterium* diphteriae NCTC 13129 (SEQ ID NO:10). Cj_Ppnk_AA: PpnK amino acid sequence of *Corynebacterium jeikeum* K411 (SEQ ID NO:11). *: identical amino acid. –: no amino acid present.

FIG. 2:

Comparison of the amino acid sequences (multiple sequence alignment) of the encoded PpnK polypeptides of various strains of the species *Corynebacterium glutamicum*.

The abbreviations have the following meaning: Cg_PpnK_AA: PpnK amino acid sequence of *Corynebacterium glutamicum* ATCC 13032 (SEQ ID NO:2). CgR_PpnK_AA: PpnK amino acid sequence of *Corynebacterium glutamicum* R (SEQ ID NO:12). Bf_PpnK_AA: PpnK amino acid sequence of *Corynebacterium glutamicum* ATCC 14067 (SEQ ID NO:4). *: identical amino acid. –: no amino acid present.

The invention claimed is:

1. A method for fermentatively producing an L-amino acid product, comprising:
   a) fermenting a modified microorganism that secretes L-lysine in a fermentation medium to form a fermentation broth, wherein:
      i) compared to an unmodified microorganism or starting strain, said modified microorganism overexpresses a polynucleotide coding for a polypeptide, wherein said polypeptide has polyphosphate-dependent $NAD^+$ kinase enzymatic activity and comprises the amino acid sequence of SEQ ID NO:2, SEQ ID NO:4 or SEQ ID NO:6;
      ii) compared to an unmodified microorganism, or starting strain, said modified microorganism produces an increased amount of L-lysine;
   b) allowing said L-lysine to accumulate in said fermentation broth and/or in the cells of said microorganism;
   c) recovering said L-amino acid product from the fermentation broth and/or cells of step b).

2. The method of claim 1, wherein said polypeptide comprises the amino acid sequence of SEQ ID NO:4 or SEQ ID NO:6.

3. The method of claim 1, wherein said polypeptide comprises the amino acid sequence of SEQ ID NO:2.

4. The method of claim 3, wherein said L-amino acid product is a solid product containing at least 10% lysine by weight.

5. The method of claim 3, wherein said microorganism is a bacterium, yeast or fungus.

6. The method of claim 3, wherein said microorganism is a bacterium of the genus *Corynebacterium* or *Escherichia*.

7. The method of claim 6, wherein said microorganism is a bacterium of the species *Corynebacterium glutamicum* or *Escherichia coli*.

8. The method of claim 7, wherein said polynucleotide is a recombinant polynucleotide.

9. The method of claim 1, wherein said polynucleotide comprises the nucleotide sequence of SEQ ID NO:1.

10. The method of claim 1, wherein said polynucleotide comprises the nucleotide sequence of SEQ ID NO:3 or SEQ ID NO:5.

11. The method of claim 1, wherein, compared to said unmodified microorganism or starting strain, said modified microorganism comprises either:
   a) an increased copy number of said polynucleotide, or
   b) a stronger promoter controlling transcription of said polynucleotide.

12. The method of claim 11, wherein said microorganism is a bacterium of the species *Corynebacterium glutamicum* and said polypeptide consists of the amino acid sequence of SEQ ID NO:2, SEQ ID NO:4 or SEQ ID NO:6.

13. The method of claim 11, wherein said microorganism is a bacterium of the species *Corynebacterium glutamicum* and said L-amino acid product is a concentrated aqueous alkaline solution of purified L-lysine or an aqueous acidic biomass-containing concentrate of L-lysine-containing fermentation broth.

14. The method of claim 11, wherein said microorganism is a bacterium of the species *Corynebacterium glutamicum* and said L-amino acid product is a solid product containing at least 10% lysine by weight.

15. The method of claim 14, wherein said solid product comprises either:
    a) a pulverulent or crystalline form of purified or pure L-lysine; or
    b) L-lysine and biomass.

16. A method for fermentatively producing an L-amino acid product, comprising:
    a) fermenting a modified microorganism that secretes L-lysine in a fermentation medium to form a fermentation broth, wherein:
        i) compared to an unmodified microorganism or starting strain, said modified microorganism overexpresses a polynucleotide coding for a polypeptide, wherein said polypeptide has polyphosphate-dependent NAD$^+$ kinase enzymatic activity and comprises an amino acid sequence that is at least 80% identical to the amino acid sequence of SEQ ID NO:2;
        ii) compared to an unmodified microorganism, or starting strain, said modified microorganism produces an increased amount of L-lysine;
    b) allowing said L-lysine to accumulate in said fermentation broth and/or in the cells of said microorganism;
    c) recovering said L-amino acid product from the fermentation broth and/or cells of step b).

17. The method of claim 16, wherein said polypeptide comprises an amino acid sequence that is at least 90% identical to the amino acid sequence of SEQ ID NO:2.

18. The method of claim 17, wherein said polypeptide comprises an amino acid sequence that is at least 96% identical to the amino acid sequence of SEQ ID NO:2.

19. The method of claim 18, wherein said polypeptide comprises an amino acid sequence that is at least 98% identical to the amino acid sequence of SEQ ID NO:2.

20. The method of claim 19, wherein said microorganism is a bacterium of the species *Corynebacterium glutamicum* and, compared to said unmodified microorganism or starting strain, said modified microorganism comprises either:
    a) an increased copy number of said polynucleotide; or
    b) a stronger promoter controlling transcription of said polynucleotide.

* * * * *

SEQUENCE LISTING

```
<160> NUMBER OF SEQ ID NOS: 12

<210> SEQ ID NO 1
<211> LENGTH: 2163
<212> TYPE: DNA
<213> ORGANISM: Corynebacterium glutamicum ATCC 13032
<220> FEATURE:
<221> NAME/KEY: CDS
<222> LOCATION: (601)..(1560)
<223> OTHER INFORMATION: Coding region of the ppnK gene

<400> SEQUENCE: 1
ggaatctttt gagcccttgg ggctcaaggt caagggccgt cgcgtgctag atgccggcgc      60
ttcgacaggc ggatttacgg acgtgttgct acgtcgagaa gcgtctgaag tagtggcagt     120
agacgtgggc tacggacagc ttatttggcg cctgcaaaac gacgaccgcg tgcgcgtggt     180
```

```
ggaccgcacc aacatcagat acatgacgct ggaagacacc ggcggagaat gcgacatgat     240
ggtgggcgat ctctcattta tttcgcttaa actcacgttg ccggcgatcg ccaaggtcct     300
aagcgacggc gctgatctat tacccatggt caagccacaa tttgaagtcg aaaagaccg     360 attgggcagt ggcggcgtgg tgcgctcacc agagttgcgc gcagaagtta ccgcggatgt     420
cgcgaaattt gcggccactt tgggcctgag cttgaagcat gttgttgcat ccccgctgcc     480
cggcccgtca ggcaacgtag aatacttcct gtggctggtt aaagatggtg gcgcttcaat     540
gccggatgac cagcaattgt cggcaatgat tgacacggct gtaaaggaag gtccgcaata     600
```

| | | | | | | | | | | | | | | | | |
|---|---|---|---|---|---|---|---|---|---|---|---|---|---|---|---|---|
| atg | act | gca | ccc | acg | aac | gct | ggg | gaa | ctc | agg | cga | gtt | ttg | ctg | gtt | 648 |
| Met | Thr | Ala | Pro | Thr | Asn | Ala | Gly | Glu | Leu | Arg | Arg | Val | Leu | Leu | Val | |
| 1 | | | | 5 | | | | | 10 | | | | | 15 | | |
| cca | cac | acc | ggg | cgt | tct | tcc | aat | att | gaa | tcc | gcc | atc | ttg | gca | gcc | 696 |
| Pro | His | Thr | Gly | Arg | Ser | Ser | Asn | Ile | Glu | Ser | Ala | Ile | Leu | Ala | Ala | |
| | | | 20 | | | | | 25 | | | | | 30 | | | |
| aag | ctg | ctc | gac | gat | gct | gga | atc | gat | gtg | agg | gtg | ctg | atc | aat | gat | 744 |
| Lys | Leu | Leu | Asp | Asp | Ala | Gly | Ile | Asp | Val | Arg | Val | Leu | Ile | Asn | Asp | |
| | | 35 | | | | | 40 | | | | | 45 | | | | |
| gca | gat | gat | cca | att | gca | gag | cac | tcc | gtt | tta | ggc | cgt | ttc | acc | cat | 792 |
| Ala | Asp | Asp | Pro | Ile | Ala | Glu | His | Ser | Val | Leu | Gly | Arg | Phe | Thr | His | |
| 50 | | | | | 55 | | | | | 60 | | | | | | |
| gtc | agg | cac | gct | gca | gac | gcc | gct | gac | ggc | gca | gaa | cta | gtt | ctg | gtg | 840 |
| Val | Arg | His | Ala | Ala | Asp | Ala | Ala | Asp | Gly | Ala | Glu | Leu | Val | Leu | Val | |
| 65 | | | | | 70 | | | | | 75 | | | | | 80 | |
| ctg | ggt | gga | gat | ggc | acc | ttc | ctc | cgc | gca | gca | gat | atg | gcc | cac | gct | 888 |
| Leu | Gly | Gly | Asp | Gly | Thr | Phe | Leu | Arg | Ala | Ala | Asp | Met | Ala | His | Ala | |
| | | | | 85 | | | | | 90 | | | | | 95 | | |
| gtt | gat | ttg | cct | gtt | ctg | ggc | atc | aac | cta | ggc | cat | gtg | gga | ttc | ttg | 936 |
| Val | Asp | Leu | Pro | Val | Leu | Gly | Ile | Asn | Leu | Gly | His | Val | Gly | Phe | Leu | |
| | | | 100 | | | | | 105 | | | | | 110 | | | |
| gct | gaa | tgg | gag | tct | gac | tca | ctt | gaa | gag | gca | ctc | aaa | cgt | gtg | atc | 984 |
| Ala | Glu | Trp | Glu | Ser | Asp | Ser | Leu | Glu | Glu | Ala | Leu | Lys | Arg | Val | Ile | |
| | | 115 | | | | | 120 | | | | | 125 | | | | |
| gac | cgc | gat | tac | cgt | att | gaa | gat | cgc | atg | acc | tta | act | gtc | gtt | gtc | 1032 |
| Asp | Arg | Asp | Tyr | Arg | Ile | Glu | Asp | Arg | Met | Thr | Leu | Thr | Val | Val | Val | |
| | 130 | | | | | 135 | | | | | 140 | | | | | |
| cta | gac | ggc | ggt | gga | gaa | gaa | atc | ggc | cga | ggc | tgg | gct | ctc | aat | gag | 1080 |
| Leu | Asp | Gly | Gly | Gly | Glu | Glu | Ile | Gly | Arg | Gly | Trp | Ala | Leu | Asn | Glu | |
| 145 | | | | | 150 | | | | | 155 | | | | | 160 | |
| gtc | agt | att | gaa | aac | tta | aac | cgc | agg | gga | gtg | ctc | gat | gca | acc | ctc | 1128 |
| Val | Ser | Ile | Glu | Asn | Leu | Asn | Arg | Arg | Gly | Val | Leu | Asp | Ala | Thr | Leu | |
| | | | | 165 | | | | | 170 | | | | | 175 | | |
| gag | gta | gat | gca | cga | cca | gtt | gct | tcc | ttt | ggt | tgc | gat | ggc | gtg | ctg | 1176 |
| Glu | Val | Asp | Ala | Arg | Pro | Val | Ala | Ser | Phe | Gly | Cys | Asp | Gly | Val | Leu | |
| | | | 180 | | | | | 185 | | | | | 190 | | | |
| att | tcc | acc | cca | acc | ggc | tcc | acc | gct | tat | gca | ttt | tcc | gcc | ggt | ggt | 1224 |
| Ile | Ser | Thr | Pro | Thr | Gly | Ser | Thr | Ala | Tyr | Ala | Phe | Ser | Ala | Gly | Gly | |
| | | 195 | | | | | 200 | | | | | 205 | | | | |
| cct | gta | ctg | tgg | cca | gaa | ctc | gat | gcc | atc | ttg | gtg | gtt | cct | aat | aac | 1272 |
| Pro | Val | Leu | Trp | Pro | Glu | Leu | Asp | Ala | Ile | Leu | Val | Val | Pro | Asn | Asn | |
| | | | 210 | | | | | 215 | | | | | 220 | | | |
| gcc | cac | gcg | ctg | ttt | acc | aaa | ccg | ctg | gtt | gtg | agc | cca | aaa | tcc | acc | 1320 |
| Ala | His | Ala | Leu | Phe | Thr | Lys | Pro | Leu | Val | Val | Ser | Pro | Lys | Ser | Thr | |
| 225 | | | | | 230 | | | | | 235 | | | | | 240 | |
| gta | gct | gtg | gaa | tcc | aat | tca | gat | act | tca | gca | gcg | atg | gcc | gtc | atg | 1368 |
| Val | Ala | Val | Glu | Ser | Asn | Ser | Asp | Thr | Ser | Ala | Ala | Met | Ala | Val | Met | |
| | | | | 245 | | | | | 250 | | | | | 255 | | |

```
gat  ggt  ttc  cgt  ccc  att  cct  atg  cct  cca  gga  tcc  cgt  gtt  gag  gtc     1416
Asp  Gly  Phe  Arg  Pro  Ile  Pro  Met  Pro  Pro  Gly  Ser  Arg  Val  Glu  Val
               260                 265                 270 acc  agg  ggt  gag  cgt  ccc  gtg  cgt  tgg  gtg  agg  ctt  gat  tct  tca  ccg     1464
Thr  Arg  Gly  Glu  Arg  Pro  Val  Arg  Trp  Val  Arg  Leu  Asp  Ser  Ser  Pro
               275                 280                 285 ttt  acc  gac  cga  ctt  gtg  agc  aaa  tta  agg  ctc  ccc  gtt  acc  ggt  tgg     1512
Phe  Thr  Asp  Arg  Leu  Val  Ser  Lys  Leu  Arg  Leu  Pro  Val  Thr  Gly  Trp
               290                 295                 300 cgg  ggt  ccg  caa  aaa  cag  gcg  gaa  aat  aaa  gat  ccc  agg  tca  gcg  ggg     1560
Arg  Gly  Pro  Gln  Lys  Gln  Ala  Glu  Asn  Lys  Asp  Pro  Arg  Ser  Ala  Gly
305            310                 315                 320 taattcgaaa accattcgaa caattttcga ggatttagaa aaaacgttcg cataaattgt               1620
tagaactgat gtacactttg aggcatgctc gtagacattg ctattgagaa cctcggagtt               1680
attccagcgg cctcagctga gttcagctca ggtttaacag tgctcaccgg tgagaccggc               1740
gccggaaaga ccatggtagt gacaggttta cgcctgttat ccggcggtcg cgccgacgct               1800
tcacgcgtgc gcacaggatc ccctcaagct gttgtggagg ggcgctttgt tacgcaaggc               1860
gtgccctgcg acattgtcga acgtgcaacc ggaatcgttt cgaacgccgg aggtgccgca               1920
gatgaaaatg gagagttttt agctgtccgt tccgtcggcg ccaacggccg ttcaaaagct               1980
catctcggtg gtcgctccgt acctgcggca acgctgtccg agttctctga tgagctgttg               2040
accatccacg gtcaaaatga ccaactccgg ttgctctccc cagaacgcca actagaggcg               2100
cttgatcgtt ttgatccaga gctggcccaa ctgcgcaaaa actacaacgc caagtacctc               2160
act                                                                              2163

<210> SEQ ID NO 2
<211> LENGTH: 320
<212> TYPE: PRT
<213> ORGANISM: Corynebacterium glutamicum ATCC 13032

<400> SEQUENCE: 2

Met  Thr  Ala  Pro  Thr  Asn  Ala  Gly  Glu  Leu  Arg  Arg  Val  Leu  Leu  Val
1                   5                   10                  15

Pro  His  Thr  Gly  Arg  Ser  Ser  Asn  Ile  Glu  Ser  Ala  Ile  Leu  Ala  Ala
               20                  25                  30

Lys  Leu  Leu  Asp  Asp  Ala  Gly  Ile  Asp  Val  Arg  Val  Leu  Ile  Asn  Asp
           35                  40                  45

Ala  Asp  Asp  Pro  Ile  Ala  Glu  His  Ser  Val  Leu  Gly  Arg  Phe  Thr  His
     50                  55                  60

Val  Arg  His  Ala  Ala  Asp  Ala  Asp  Gly  Ala  Glu  Leu  Val  Leu  Val
65                  70                  75                  80

Leu  Gly  Gly  Asp  Gly  Thr  Phe  Leu  Arg  Ala  Ala  Asp  Met  Ala  His  Ala
                    85                  90                  95

Val  Asp  Leu  Pro  Val  Leu  Gly  Ile  Asn  Leu  Gly  His  Val  Gly  Phe  Leu
               100                 105                 110

Ala  Glu  Trp  Glu  Ser  Asp  Ser  Leu  Glu  Glu  Ala  Leu  Lys  Arg  Val  Ile
           115                 120                 125

Asp  Arg  Asp  Tyr  Arg  Ile  Glu  Asp  Arg  Met  Thr  Leu  Thr  Val  Val  Val
     130                 135                 140

Leu  Asp  Gly  Gly  Gly  Glu  Ile  Gly  Arg  Gly  Trp  Ala  Leu  Asn  Glu
145                 150                 155                 160

Val  Ser  Ile  Glu  Asn  Leu  Asn  Arg  Arg  Gly  Val  Leu  Asp  Ala  Thr  Leu
                    165                 170                 175
```

```
Glu Val Asp Ala Arg Pro Val Ala Ser Phe Gly Cys Asp Gly Val Leu
            180                 185                 190

Ile Ser Thr Pro Thr Gly Ser Thr Ala Tyr Ala Phe Ser Ala Gly Gly
        195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225                 230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala Gly
305                 310                 315                 320

<210> SEQ ID NO 3
<211> LENGTH: 963
<212> TYPE: DNA
<213> ORGANISM: Corynebacterium glutamicum ATCC 14067
<220> FEATURE:
<221> NAME/KEY: CDS
<222> LOCATION: (1)..(960)
<223> OTHER INFORMATION: Coding region of the ppnK gene

<400> SEQUENCE: 3 atg act gca tcc acg aac gct ggg gaa ctc agg cga gtt ttg ctg gtt      48
Met Thr Ala Ser Thr Asn Ala Gly Glu Leu Arg Arg Val Leu Leu Val
1               5                   10                  15 cca cac acc ggg cgt tct tcc aat att gaa tcc gcc atc ttg gca gcc      96
Pro His Thr Gly Arg Ser Ser Asn Ile Glu Ser Ala Ile Leu Ala Ala
                20                  25                  30 aag ctg ctc gat gat gcg gga atc gat gtg agg gtg ctg atc aat gat     144
Lys Leu Leu Asp Asp Ala Gly Ile Asp Val Arg Val Leu Ile Asn Asp
            35                  40                  45 gca gat gat cca att gca gag cac ccc gtt tta ggc cgt ttc acc cat     192
Ala Asp Asp Pro Ile Ala Glu His Pro Val Leu Gly Arg Phe Thr His
        50                  55                  60 gtc agg cac gct gcc gac gct gct gac ggc gca gaa cta gtt ctg gtg     240
Val Arg His Ala Ala Asp Ala Ala Asp Gly Ala Glu Leu Val Leu Val
65                  70                  75                  80 ctg ggt gga gat ggc acc ttc ctc cgc gca gca gat atg gcc cac gct     288
Leu Gly Gly Asp Gly Thr Phe Leu Arg Ala Ala Asp Met Ala His Ala
                85                  90                  95 gtt gat ttg cct gtt ctg ggc atc aac cta ggc cat gtg gga ttc ttg     336
Val Asp Leu Pro Val Leu Gly Ile Asn Leu Gly His Val Gly Phe Leu
            100                 105                 110 gct gaa tgg gag tct gac tca ctt gaa gag gca ctc aaa cgt gtg atc     384
Ala Glu Trp Glu Ser Asp Ser Leu Glu Glu Ala Leu Lys Arg Val Ile
        115                 120                 125 gac cgc gat tac cgt att gaa gat cgc atg acc tta aat gtc gtt gtc     432
Asp Arg Asp Tyr Arg Ile Glu Asp Arg Met Thr Leu Asn Val Val Val
    130                 135                 140 cta gac ggc ggt gga gaa gaa atc ggc cga gga tgg gct ctc aat gag     480
Leu Asp Gly Gly Gly Glu Glu Ile Gly Arg Gly Trp Ala Leu Asn Glu
145                 150                 155                 160
```

```
gtc agc atc gaa aac tta aac cgc agg gga gtg ctc gat gca acc ctc         528
Val Ser Ile Glu Asn Leu Asn Arg Arg Gly Val Leu Asp Ala Thr Leu
            165                 170                 175 gag gta gat gca cga cca gtt gct tcc ttt ggt tgc gat ggc gtg ctg         576
Glu Val Asp Ala Arg Pro Val Ala Ser Phe Gly Cys Asp Gly Val Leu
        180                 185                 190 att tcc acc cca acc ggc tcc acc gct tat gca ttt tcc gcc ggt ggt         624
Ile Ser Thr Pro Thr Gly Ser Thr Ala Tyr Ala Phe Ser Ala Gly Gly
    195                 200                 205 cct gta ctg tgg cca gaa ctc gat gcc atc ttg gtg gtt cct aat aac         672
Pro Val Leu Trp Pro Glu Leu Asp Ala Ile Leu Val Val Pro Asn Asn
210                 215                 220 gcc cac gcg ctg ttt acc aaa ccg ctg gtt gtg agc cca aaa tcc acc         720
Ala His Ala Leu Phe Thr Lys Pro Leu Val Val Ser Pro Lys Ser Thr
225                 230                 235                 240 gta gct gtg gaa tcc aat tca gat act tca gca gcg atg gcc gtc atg         768
Val Ala Val Glu Ser Asn Ser Asp Thr Ser Ala Ala Met Ala Val Met
                245                 250                 255 gat ggt ttc cgt ccc att cct atg cct cca gga tcc cgt gtt gag gtc         816
Asp Gly Phe Arg Pro Ile Pro Met Pro Pro Gly Ser Arg Val Glu Val
            260                 265                 270 acc agg ggt gag cgt ccc gtg cgt tgg gtg agg ctt gat tct tca ccg         864
Thr Arg Gly Glu Arg Pro Val Arg Trp Val Arg Leu Asp Ser Ser Pro
        275                 280                 285 ttt acc gac cga ctt gtg agc aaa tta agg ctc ccc gtt acc ggt tgg         912
Phe Thr Asp Arg Leu Val Ser Lys Leu Arg Leu Pro Val Thr Gly Trp
    290                 295                 300 cgg ggt ccg caa aaa cag gcg gaa aat aaa gat ccc agg tca gcg ggg         960
Arg Gly Pro Gln Lys Gln Ala Glu Asn Lys Asp Pro Arg Ser Ala Gly
305                 310                 315                 320 taa                                                                     963

<210> SEQ ID NO 4
<211> LENGTH: 320
<212> TYPE: PRT
<213> ORGANISM: Corynebacterium glutamicum ATCC 14067

<400> SEQUENCE: 4

Met Thr Ala Ser Thr Asn Ala Gly Glu Leu Arg Arg Val Leu Leu Val
1               5                   10                  15

Pro His Thr Gly Arg Ser Ser Asn Ile Glu Ser Ala Ile Leu Ala Ala
            20                  25                  30

Lys Leu Leu Asp Asp Ala Gly Ile Asp Val Arg Val Leu Ile Asn Asp
        35                  40                  45

Ala Asp Asp Pro Ile Ala Glu His Pro Val Leu Gly Arg Phe Thr His
    50                  55                  60

Val Arg His Ala Ala Asp Ala Asp Gly Ala Glu Leu Val Leu Val
65                  70                  75                  80

Leu Gly Gly Asp Gly Thr Phe Leu Arg Ala Ala Asp Met Ala His Ala
                85                  90                  95

Val Asp Leu Pro Val Leu Gly Ile Asn Leu Gly His Val Gly Phe Leu
            100                 105                 110

Ala Glu Trp Glu Ser Asp Ser Leu Glu Ala Leu Lys Arg Val Ile
        115                 120                 125

Asp Arg Asp Tyr Arg Ile Glu Asp Arg Met Thr Leu Asn Val Val Val
    130                 135                 140

Leu Asp Gly Gly Gly Glu Glu Ile Gly Arg Gly Trp Ala Leu Asn Glu
145                 150                 155                 160
```

```
Val Ser Ile Glu Asn Leu Asn Arg Arg Gly Val Leu Asp Ala Thr Leu
            165                 170                 175

Glu Val Asp Ala Arg Pro Val Ala Ser Phe Gly Cys Asp Gly Val Leu
        180                 185                 190

Ile Ser Thr Pro Thr Gly Ser Thr Ala Tyr Ala Phe Ser Ala Gly Gly
            195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225                 230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala Gly
305                 310                 315                 320

<210> SEQ ID NO 5
<211> LENGTH: 963
<212> TYPE: DNA
<213> ORGANISM: Corynebacterium glutamicum ATCC 13869
<220> FEATURE:
<221> NAME/KEY: CDS
<222> LOCATION: (1)..(960)
<223> OTHER INFORMATION: Coding region of the ppnK gene

<400> SEQUENCE: 5 atg act gca ccc acg aac gct ggg gaa ctc agg cga gtt ttg ctg gtt      48
Met Thr Ala Pro Thr Asn Ala Gly Glu Leu Arg Arg Val Leu Leu Val
1               5                   10                  15 cca cac acc ggg cgt tct tcc aat att gaa tcc gcc atc ttg gca gcc      96
Pro His Thr Gly Arg Ser Ser Asn Ile Glu Ser Ala Ile Leu Ala Ala
            20                  25                  30 aag ctg ctc gac gat gct gga atc gat gtg agg gtg ctg atc aat gat     144
Lys Leu Leu Asp Asp Ala Gly Ile Asp Val Arg Val Leu Ile Asn Asp
        35                  40                  45 gca gat gat cca att gca gag cac ccc gtt tta ggc cgt ttc acc cat     192
Ala Asp Asp Pro Ile Ala Glu His Pro Val Leu Gly Arg Phe Thr His
    50                  55                  60 gtc agg cac gct gcc gac gct gct gac ggc gca gaa cta gtt ctg gtg     240
Val Arg His Ala Ala Asp Ala Ala Asp Gly Ala Glu Leu Val Leu Val
65                  70                  75                  80 ctg ggt gga gat ggc acc ttc ctc cgc gca gca gat atg gcc cac gct     288
Leu Gly Gly Asp Gly Thr Phe Leu Arg Ala Ala Asp Met Ala His Ala
                85                  90                  95 gtt gat ttg cct gtt ctg ggc atc aac cta ggc cat gtg gga ttc ttg     336
Val Asp Leu Pro Val Leu Gly Ile Asn Leu Gly His Val Gly Phe Leu
            100                 105                 110 gct gaa tgg gag tct gac tca ctt gaa gag gca ctc aaa cgt gtg atc     384
Ala Glu Trp Glu Ser Asp Ser Leu Glu Glu Ala Leu Lys Arg Val Ile
        115                 120                 125 gac cgc gat tac cgt att gaa gat cgc atg acc tta act gtc gtt gtc     432
Asp Arg Asp Tyr Arg Ile Glu Asp Arg Met Thr Leu Thr Val Val Val
    130                 135                 140
```

```
cta gac ggc ggt gga gaa gaa atc ggc cga ggc tgg gct ctc aat gag        480
Leu Asp Gly Gly Gly Glu Glu Ile Gly Arg Gly Trp Ala Leu Asn Glu
145                 150                 155                 160 gtc agt att gaa aac tta aac cgc agg gga gtg ctc gat gca acc ctc        528
Val Ser Ile Glu Asn Leu Asn Arg Arg Gly Val Leu Asp Ala Thr Leu
                165                 170                 175 gag gta gat gca cga cca gtt gct tcc ttt ggt tgc gat ggc gtg ctg        576
Glu Val Asp Ala Arg Pro Val Ala Ser Phe Gly Cys Asp Gly Val Leu
            180                 185                 190 att tcc acc cca acc ggc tcc acc gct tat gca ttt tcc gcc ggt ggt        624
Ile Ser Thr Pro Thr Gly Ser Thr Ala Tyr Ala Phe Ser Ala Gly Gly
        195                 200                 205 cct gta ctg tgg cca gaa ctc gat gcc atc ttg gtg gtt cct aat aac        672
Pro Val Leu Trp Pro Glu Leu Asp Ala Ile Leu Val Val Pro Asn Asn
    210                 215                 220 gcc cac gcg ctg ttt acc aaa ccg ctg gtt gtg agc cca aaa tcc acc        720
Ala His Ala Leu Phe Thr Lys Pro Leu Val Val Ser Pro Lys Ser Thr
225                 230                 235                 240 gta gct gtg gaa tcc aat tca gat act tca gca gcg atg gcc gtc atg        768
Val Ala Val Glu Ser Asn Ser Asp Thr Ser Ala Ala Met Ala Val Met
                245                 250                 255 gat ggt ttc cgt ccc att cct atg cct cca gga tcc cgt gtt gag gtc        816
Asp Gly Phe Arg Pro Ile Pro Met Pro Pro Gly Ser Arg Val Glu Val
            260                 265                 270 acc agg ggt gag cgt ccc gtg cgt tgg gtg agg ctt gat tct tca ccg        864
Thr Arg Gly Glu Arg Pro Val Arg Trp Val Arg Leu Asp Ser Ser Pro
        275                 280                 285 ttt acc gac cga ctt gtg agc aaa tta agg ctc ccc gtt acc ggt tgg        912
Phe Thr Asp Arg Leu Val Ser Lys Leu Arg Leu Pro Val Thr Gly Trp
    290                 295                 300 cgg ggt ccg caa aaa cag gcg gaa aat aaa gat ccc agg tca gcg ggg        960
Arg Gly Pro Gln Lys Gln Ala Glu Asn Lys Asp Pro Arg Ser Ala Gly
305                 310                 315                 320 taa                                                                    963

<210> SEQ ID NO 6
<211> LENGTH: 320
<212> TYPE: PRT
<213> ORGANISM: Corynebacterium glutamicum ATCC 13869

<400> SEQUENCE: 6

Met Thr Ala Pro Thr Asn Ala Gly Glu Leu Arg Arg Val Leu Leu Val
1               5                   10                  15

Pro His Thr Gly Arg Ser Ser Asn Ile Glu Ser Ala Ile Leu Ala Ala
                20                  25                  30

Lys Leu Leu Asp Asp Ala Gly Ile Asp Val Arg Val Leu Ile Asn Asp
            35                  40                  45

Ala Asp Asp Pro Ile Ala Glu His Pro Val Leu Gly Arg Phe Thr His
        50                  55                  60

Val Arg His Ala Ala Asp Ala Ala Asp Gly Ala Glu Leu Val Leu Val
65                  70                  75                  80

Leu Gly Gly Asp Gly Thr Phe Leu Arg Ala Ala Asp Met Ala His Ala
                85                  90                  95

Val Asp Leu Pro Val Leu Gly Ile Asn Leu Gly His Val Gly Phe Leu
            100                 105                 110

Ala Glu Trp Glu Ser Asp Ser Leu Glu Glu Ala Leu Lys Arg Val Ile
        115                 120                 125

Asp Arg Asp Tyr Arg Ile Glu Asp Arg Met Thr Leu Thr Val Val Val
```

-continued

```
                130             135             140
Leu Asp Gly Gly Gly Glu Glu Ile Gly Arg Gly Trp Ala Leu Asn Glu
145                 150                 155                 160

Val Ser Ile Glu Asn Leu Asn Arg Arg Gly Val Leu Asp Ala Thr Leu
                165                 170                 175

Glu Val Asp Ala Arg Pro Val Ala Ser Phe Gly Cys Asp Gly Val Leu
            180                 185                 190

Ile Ser Thr Pro Thr Gly Ser Thr Ala Tyr Ala Phe Ser Ala Gly Gly
        195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225                 230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala Gly
305                 310                 315                 320

<210> SEQ ID NO 7
<211> LENGTH: 44
<212> TYPE: DNA
<213> ORGANISM: Corynebacterium glutamicum
<220> FEATURE:
<221> NAME/KEY: misc_feature
<222> LOCATION: (1)..(44)
<223> OTHER INFORMATION: Primer ppnK_fw
<220> FEATURE:
<221> NAME/KEY: misc_feature
<222> LOCATION: (25)..(27)
<223> OTHER INFORMATION: Start codon

<400> SEQUENCE: 7
ggatgtcgac aaggagatat agatatgact gcacccacga acgc        44

<210> SEQ ID NO 8
<211> LENGTH: 28
<212> TYPE: DNA
<213> ORGANISM: Corynebacterium glutamicum
<220> FEATURE:
<221> NAME/KEY: misc_feature
<222> LOCATION: (1)..(28)
<223> OTHER INFORMATION: Primer ppnK_rv
<220> FEATURE:
<221> NAME/KEY: misc_feature
<222> LOCATION: (11)..(13)
<223> OTHER INFORMATION: Stop codon

<400> SEQUENCE: 8
gccatctaga ttaccccgct gacctggg        28

<210> SEQ ID NO 9
<211> LENGTH: 318
<212> TYPE: PRT
<213> ORGANISM: Corynebacterium efficiens YS-314
<220> FEATURE:
<221> NAME/KEY: MISC_FEATURE
<222> LOCATION: (1)..(318)
```

<223> OTHER INFORMATION: ppnK amino acid sequence

<400> SEQUENCE: 9

```
Met Thr Glu Thr Thr Glu Arg Ile Val Leu Leu Val Pro His Thr Gly
1               5                   10                  15

Arg Ser Ser Asn Ile Glu Ser Ala Val Leu Ala Ala Glu His Leu Asp
            20                  25                  30

Arg Ala Gly Ile Thr Val Arg Val Leu Val Asn Glu Glu Asp Asp Pro
        35                  40                  45

Ile Lys Thr His Pro Val Leu Gly Arg Phe Glu His Val Ile His Ser
    50                  55                  60

Arg Thr Ala Ala Glu Gly Ala Glu Leu Val Leu Val Leu Gly Gly Asp
65                  70                  75                  80

Gly Thr Phe Leu Arg Ala Ala Asp Leu Ala His Ala Val Asp Leu Pro
                85                  90                  95

Val Leu Gly Ile Asn Leu Gly His Val Gly Phe Leu Ala Glu Trp Glu
            100                 105                 110

Ser Asp Ser Leu Glu Asp Ala Val Lys Arg Val Ile Asp Cys Asp Tyr
        115                 120                 125

Arg Val Glu Asp Arg Met Thr Leu Asp Val Ile Val Arg Asp Ser Asp
    130                 135                 140

Leu Glu Val Ile Gly Arg Gly Trp Ala Leu Asn Glu Val Ser Val Glu
145                 150                 155                 160

Asn Leu Asn Arg Arg Gly Val Leu Asp Ala Thr Leu Glu Val Asp Phe
                165                 170                 175

Arg Pro Val Ala Ser Phe Gly Cys Asp Gly Val Leu Ile Ser Thr Pro
            180                 185                 190

Thr Gly Ser Thr Ala Tyr Ala Phe Ser Ala Gly Gly Pro Val Leu Trp
        195                 200                 205

Pro Glu Leu Asp Ala Ile Leu Val Val Pro Asn Asn Ala His Ala Leu
    210                 215                 220

Phe Thr Lys Pro Leu Val Val Ser Pro Arg Ser Thr Val Ala Val Glu
225                 230                 235                 240

Ser Met Ser Gly Thr Ser Pro Ala Met Ala Val Met Asp Gly Phe Arg
                245                 250                 255

Pro Ile Pro Met Pro Pro Gly Ser Arg Val Glu Ile Val Arg Gly Lys
            260                 265                 270

Arg Pro Val Arg Trp Val Arg Leu Asp Ser Leu Pro Phe Thr Asp Arg
        275                 280                 285

Leu Val His Lys Leu Arg Leu Pro Val Val Gly Trp Arg Gly Pro Asp
    290                 295                 300

Lys Gln Lys Glu Leu Leu Asp Ala Glu Thr Pro Asp Gln Pro
305                 310                 315
```

<210> SEQ ID NO 10
<211> LENGTH: 317
<212> TYPE: PRT
<213> ORGANISM: Corynebacterium diphteriae NCTC 13129
<220> FEATURE:
<221> NAME/KEY: MISC_FEATURE
<222> LOCATION: (1)..(317)
<223> OTHER INFORMATION: ppnK amino acid sequence

<400> SEQUENCE: 10

```
Met Thr Ile Asp Cys His Glu Asp Arg Arg Val Leu Leu Val Pro His
1               5                   10                  15
```

```
Thr Gly Arg Pro Gln Asn Val Ala Ser Ala Ala Leu Ala Ala Glu Leu
                20                  25                  30

Leu Asp Asp Ser Gly Val Gly Val Arg Val Leu Val Pro Ala Glu Asp
             35                  40                  45

Thr Thr Val Ala Thr His Pro Val Leu Gly Gln Phe Glu Arg Val Ser
         50                  55                  60

His Ser Pro Gln Ala Thr Gln Ser Val Asp Leu Val Leu Val Leu Gly
 65                  70                  75                  80

Gly Asp Gly Thr Phe Leu Arg Ala Ala Asp Leu Ala His Gly Ala Asp
                 85                  90                  95

Leu Pro Val Leu Gly Ile Asn Leu Gly His Val Gly Phe Leu Ala Glu
            100                 105                 110

Trp Glu Lys Asp Ser Leu Asp Glu Ala Val Arg Arg Val Thr Lys Gly
        115                 120                 125

Ser Phe Arg Ile Glu Glu Arg Met Thr Leu Asp Val Ser Val Tyr Asp
130                 135                 140

Ser Asn Gly Thr Ala Ile Gly Arg Gly Trp Ala Leu Asn Glu Val Ser
145                 150                 155                 160

Ile Glu Asn Ser Asn Arg Ser Gly Val Leu Asp Ala Thr Leu Glu Ile
                165                 170                 175

Asp Ser Arg Pro Val Ser Ser Phe Gly Cys Asp Gly Ile Ile Val Ser
            180                 185                 190

Thr Pro Thr Gly Ser Thr Ala Tyr Ala Phe Ser Ala Gly Gly Pro Val
        195                 200                 205

Leu Trp Pro Glu Leu Asp Ala Ile Leu Val Val Pro Asn Asn Ala His
    210                 215                 220

Ala Leu Phe Thr Lys Pro Leu Val Val Ser Pro Arg Ser Ser Val Ala
225                 230                 235                 240

Val Glu Ser His Pro Ser Ala Phe Pro Ala Thr Ala Val Met Asp Gly
                245                 250                 255

Phe Arg Ser Ile Ser Val Pro Pro Gly Ala Arg Val Glu Val Lys Arg
            260                 265                 270

Gly Ser Arg Ser Ile Lys Trp Val Arg Leu Asp Asp Ile Pro Phe Thr
        275                 280                 285

Asp Arg Leu Val Thr Lys Leu Arg Leu Pro Val Glu Gly Trp Arg Gly
    290                 295                 300

Pro Lys Asn Met Ile Pro Gln Ile Asn Pro His Ser Ala
305                 310                 315

<210> SEQ ID NO 11
<211> LENGTH: 329
<212> TYPE: PRT
<213> ORGANISM: Corynebacterium jeikeum K411
<220> FEATURE:
<221> NAME/KEY: MISC_FEATURE
<222> LOCATION: (1)..(329)
<223> OTHER INFORMATION: ppnK amino acid sequence

<400> SEQUENCE: 11

Met Thr Thr Pro Gly Thr Asp His Asn Ala Asp Gln Gly Ala Asp Ser
 1               5                  10                  15

Gly Asp Lys Ala Thr Lys Ala Ala Ser Gly Ala Gln Thr Glu Arg Glu
                20                  25                  30

Val Leu Leu Val Ala His Thr Gly Val His Glu Asn Leu Gly Leu Ala
             35                  40                  45

Ala Glu Ala Ala Ser Arg Leu Gln Lys Gly Gly Ile Asn Val Arg Val
```

```
            50                  55                  60
Met Ala Thr Ala Asp Pro Ala Pro Val Ala Arg His Glu Val Leu Gly
 65                  70                  75                  80

Arg Phe Lys Arg Phe Gly His Thr Lys Glu Ala Ala Thr Gly Val Glu
                     85                  90                  95

Met Val Ile Val Leu Gly Gly Asp Gly Thr Phe Leu Arg Ala Ala Asp
                100                 105                 110

Ile Ala His Ser Ala Asp Val Pro Val Leu Gly Ile Asn Met Gly His
            115                 120                 125

Ile Gly Phe Leu Ala Glu Trp Glu Gln Glu Ser Leu Gln Glu Ala Val
        130                 135                 140

Asp Arg Val Ile Asp Arg Asp Tyr Arg Ile Glu Asp Arg Met Thr Leu
145                 150                 155                 160

Ser Ile Thr Ala Arg Asp Met Asp Gly Arg Val Leu Gly Thr Gly Trp
                    165                 170                 175

Ala Leu Asn Glu Cys Ser Val Glu Asn Leu Asn Arg Gln Gly Val Leu
                180                 185                 190

Asp Thr Ile Leu Glu Val Asp Glu Arg Pro Val Ser Ser Phe Gly Cys
            195                 200                 205

Asp Gly Val Leu Val Ser Thr Pro Thr Gly Ser Thr Ala Tyr Ala Phe
        210                 215                 220

Ser Ala Gly Gly Pro Val Leu Trp Pro Glu Leu Asp Ala Ile Leu Val
225                 230                 235                 240

Val Thr Ser Asn Ala His Thr Leu Phe Ser Arg Pro Leu Val Val Ser
                    245                 250                 255

Pro Asn Ser Met Val Ala Val Glu Thr Asn Pro Ser Thr Ser Pro Ala
                260                 265                 270

Thr Val Val Met Asp Gly Phe Arg Gln Ile His Met Pro Pro Gly Ala
            275                 280                 285

Arg Val Glu Ile Arg Arg Gly Pro Gln Pro Val Arg Trp Val Arg Leu
        290                 295                 300

Asp Ser Ala Pro Phe Thr Asp Arg Leu Val His Lys Phe Arg Leu Pro
305                 310                 315                 320

Val Thr Gly Trp Arg Gly Pro Arg His
                325

<210> SEQ ID NO 12
<211> LENGTH: 320
<212> TYPE: PRT
<213> ORGANISM: Corynebacterium glutamicum R
<220> FEATURE:
<221> NAME/KEY: MISC_FEATURE
<222> LOCATION: (1)..(320)
<223> OTHER INFORMATION: ppnK amino acid sequence

<400> SEQUENCE: 12

Met Thr Ala Pro Thr Asn Ala Gly Glu Leu Arg Arg Val Leu Leu Val
 1                5                  10                  15

Pro His Thr Gly Arg Ser Ser Asn Ile Glu Ser Ala Ile Leu Ala Ala
                20                  25                  30

Lys Leu Leu Asp Asp Ala Gly Ile Asp Val Arg Val Leu Ile Asn Asp
            35                  40                  45

Ala Asp Asp Pro Ile Ala Glu His Pro Val Leu Gly Arg Phe Thr His
        50                  55                  60

Val Arg His Ala Ala Asp Ala Ala Glu Gly Ala Glu Leu Val Leu Val
65                  70                  75                  80
```

```
Leu Gly Gly Asp Gly Thr Phe Leu Arg Ala Ala Asp Met Ala His Ala
                85                  90                  95

Val Asp Leu Pro Val Leu Gly Ile Asn Leu Gly His Val Gly Phe Leu
            100                 105                 110

Ala Glu Trp Glu Ser Asp Ser Leu Glu Glu Ala Leu Lys Arg Val Ile
        115                 120                 125

Asp Arg Asp Tyr Arg Ile Glu Asp Arg Met Thr Leu Thr Val Val Val
    130                 135                 140

Leu Asp Gly Gly Glu Glu Ile Gly Arg Gly Trp Ala Leu Asn Glu
145             150                 155                 160

Val Ser Ile Glu Asn Leu Asn Arg Arg Gly Val Leu Asp Ala Thr Leu
                165                 170                 175

Glu Val Asp Ala Arg Pro Val Ala Ser Phe Gly Cys Asp Gly Val Leu
            180                 185                 190

Ile Ser Thr Pro Thr Gly Ser Thr Ala Tyr Ala Phe Ser Ala Gly Gly
        195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225             230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala Gly
305             310                 315                 320
```